US012758159B2

(12) United States Patent
Broderick et al.

(10) Patent No.: US 12,758,159 B2
(45) Date of Patent: Oct. 13, 2026

(54) SYSTEM AND METHOD FOR IDENTIFYING AND INTEGRATING DIGITAL SSL MOVEMENT BIOMARKERS

(71) Applicant: Beneufit, Inc., Kentfield, CA (US)

(72) Inventors: Jeffery Broderick, San Anselmo, CA (US); Ugenteraan Manogaran, Cyberjaya (MY)

(73) Assignee: Beneufit, Inc., Kentfield, CA (US)

( * ) Notice: Subject to any disclaimer, the term of this patent is extended or adjusted under 35 U.S.C. 154(b) by 0 days.

(21) Appl. No.: 19/093,725

(22) Filed: Mar. 28, 2025

(65) Prior Publication Data

US 2025/0248661 A1 Aug. 7, 2025

Related U.S. Application Data

(60) Provisional application No. 63/571,663, filed on Mar. 29, 2024.

(51) Int. Cl.
*A61B 5/00* (2006.01)
*A61B 5/11* (2006.01)
(Continued)

(52) U.S. Cl.
CPC .......... *A61B 5/7267* (2013.01); *A61B 5/0077* (2013.01); *A61B 5/1128* (2013.01); (Continued)

(58) Field of Classification Search
CPC ... A61B 5/7267; A61B 5/0077; A61B 5/1128; A61B 2576/00; G06T 7/0012;
(Continued)

(56) References Cited

U.S. PATENT DOCUMENTS

2016/0089089 A1* 3/2016 Kakkar .................. G16H 40/67 600/484
2018/0108440 A1* 4/2018 Stevens .................. G16H 50/20
(Continued)

OTHER PUBLICATIONS

Edgar et al. "A Parkinsonian Digital Biomarker Learned as an Anomaly Deep Generative Representation"; 44th Annual International Conference of the IEEE Engineering in Medicine & Biology Society (EMBC) Scottish Event Campus, Glasgow, UK, Jul. 11-15, pp. 4188-4191; 2022 (Year: 2022).*
(Continued)

*Primary Examiner* — Dixomara Vargas
(74) *Attorney, Agent, or Firm* — Steven A. Nielsen; www.NielsenPatents.com

(57) ABSTRACT

Disclosed examples relate to a system and method for creating and integrating self-supervised learning (SSL) digital movement biomarkers into electronic health records (EHRs) for enhanced diagnostic support and treatment monitoring, particularly for rare diseases and movement disorders. Example systems employ SSL techniques to analyze video data, tracking body key points and extracting kinematic data without the need for human-labeled annotations. Disclosed examples generate digital movement biomarker profiles that quantify symptoms and track disease progression, facilitating the objective measurement of drug impacts on symptoms. Example systems include components for video processing, compliance checking, pose estimation, context analysis, kinematic measurement, and classification. The digital movement biomarker profiles are stored securely and made accessible for clinical use, offering a novel approach to personalized medicine by enabling the identification of disorder-specific traits and symptom similarities across different disorders.

19 Claims, 24 Drawing Sheets
(10 of 24 Drawing Sheet(s) Filed in Color)

(51) Int. Cl.

| | |
|---|---|
| ***G06T 7/00*** | (2017.01) |
| ***G06T 7/246*** | (2017.01) |
| ***G06T 7/70*** | (2017.01) |
| ***G16H 10/20*** | (2018.01) |
| ***G16H 10/60*** | (2018.01) |

(52) U.S. Cl.
CPC ............ *G06T 7/0012* (2013.01); *G06T 7/246* (2017.01); *G06T 7/70* (2017.01); *G16H 10/20* (2018.01); *G16H 10/60* (2018.01); *A61B 2576/00* (2013.01); *G06T 2200/24* (2013.01); *G06T 2207/10016* (2013.01); *G06T 2207/20081* (2013.01); *G06T 2207/30196* (2013.01)

(58) Field of Classification Search
CPC ....... G06T 7/246; G06T 7/70; G06T 2200/24; G06T 2207/10016; G06T 2207/20081; G06T 2207/30196; G16H 10/20; G16H 10/60
See application file for complete search history.

(56) References Cited

U.S. PATENT DOCUMENTS

| | | | | |
|---|---|---|---|---|
| 2022/0330879 | A1* | 10/2022 | Faisal | G16H 20/30 |
| 2023/0395235 | A1* | 12/2023 | Rajput | A61B 5/162 |
| 2023/0419730 | A1* | 12/2023 | Yerushalmy | G06V 10/70 |
| 2024/0069645 | A1* | 2/2024 | Rollinger | G06F 3/017 |
| 2024/0203592 | A1* | 6/2024 | Jeong | G16H 20/70 |
| 2024/0363238 | A1* | 10/2024 | Pandipati | G16H 40/63 |
| 2025/0157258 | A1* | 5/2025 | Robertson | G06T 7/10 |
| 2025/0218538 | A1* | 7/2025 | Selega | G16B 40/00 |

OTHER PUBLICATIONS

Noumeir; "Active Learning of the HL7 Medical Standard"; Journal of Digital Imaging (2019) 32:354-361 (Year: 2019).*

* cited by examiner

Child standing with walker

Child standing against wall

Child sitting in chair

Child sitting in chair swing

Child sitting supported by adult

Child lying supported by adult

Child sitting in wheelchair

Adult sitting in chair

Child standing supported by adult

Profile Example:

*Profile Value = 70 units symptom A + 40 units symptom B + 5 units symptom C*

SYSTEM AND METHOD FOR IDENTIFYING AND INTEGRATING DIGITAL SSL MOVEMENT BIOMARKERS

RELATED PATENT APPLICATION AND INCORPORATION BY REFERENCE

This is a utility application based upon U.S. patent application Ser. No. 63/571,663 filed on Mar. 29, 2024. This related application is incorporated herein by reference and made a part of this application. If any conflict arises between the disclosure of the invention in this utility application and that in the related provisional application, the disclosure in this utility application shall govern. Moreover, the inventor (s) incorporate herein by reference any and all patents, patent applications, and other documents hard copy or electronic, cited or referred to in this application.

TECHNICAL FIELD

The present invention relates generally to the field of digital health and, more specifically, to a system and method for identifying and integrating self-supervised learning (SSL) digital movement biomarkers for enhanced diagnostic support. Some examples identify and utilize digital movement biomarkers derived from video analysis using SSL techniques. Some examples provide systems and methods for integrating self-supervised learning digital movement biomarkers with electronic health records for enhanced use and application of appropriate medication and diagnostic support.

BACKGROUND

The development of digital movement biomarkers has become increasingly important in the medical field, particularly for the diagnosis and monitoring of diseases. Traditional biomarkers often rely on subjective outcome measures, which can lack sensitivity and are prone to human error. This is especially problematic in the context of rare diseases, where small patient populations and variability in disease presentation pose significant challenges to clinical research and the development of appropriate outcome measures.

In the realm of movement disorders and rare genetic conditions, observational clinical outcome measures are often inadequate. They may fail to detect subtle but clinically significant changes in a patient's condition, and the administration of these measures typically requires the presence of a trained expert, which can be inconvenient and inaccessible for many patients.

Some additional challenges face practitioners and stakeholders treating rare disease. For example, a lack of disease-specific measures, methods of identification, or treatments currently exists. Many rare diseases do not have well-established, disease specific outcome measures. In some cases, researchers and healthcare providers may have to rely on generic or surrogate measures that may not accurately capture the disease's unique characteristics and progression. Additionally, small sample sizes can present challenges. Rare diseases affect a limited number of individuals, leading to small patient populations available for research. This can hinder the ability to collect sufficient data to develop robust outcome measures or to conduct meaningful clinical trials.

There is also a variability in disease presentation. For example, rare diseases can exhibit significant variability in their clinical presentation, even among individuals with the same genetic mutation. This heterogeneity can complicate the development of standardized outcome measures that account for the full spectrum of disease manifestations. Accessibility to appropriate expertise can also present challenges. Patients with rare diseases may face difficulties in accessing healthcare providers and researchers with expertise in their condition. This can affect the quality of data collection and the development of relevant outcome measures.

Regulatory hurdles can also be difficult to overcome. Regulatory agencies such as the U.S. Food and Drug Administration (FDA) and the European Medicines Agency (EMA) have specific requirements for outcome measures in clinical trials. Meeting these requirements for rare diseases can be particularly challenging in the face of the difficult issues discussed above.

Machine learning models, including those based on supervised learning, have been employed to analyze video data for the purpose of health assessment. However, these models often require extensive labeled datasets for training, which are difficult and costly to obtain in the healthcare domain. Moreover, supervised learning models may not adequately account for the temporal context and object interactions present in video data, leading to less accurate and less meaningful analysis.

In this regard, a machine learning model may not necessarily understand the context of a video and therefor the resulting data becomes less useful. For instance, a person standing up and leaning against a wall will have less postural sway than a person standing in the middle of a room. In neurodevelopment disease use cases, there is a challenge in requiring a person to perform a specific task such as standing still. Many rare disease children are not able to perform a task consistently or at all. A child may not be able to stand or sit still because of the effects of the disorder. A child walking with the aid of a walker will be more stable than a child walking aided even though the child requiring the walker is more disabled. The context of the video can be as important as measuring the body movement itself.

BRIEF SUMMARY

Some examples seek to address the aforementioned challenges by providing systems and methods for creating Self-Supervised (SSL) digital movement biomarkers. Disclosed examples leverage SSL, a machine learning paradigm that does not require human-labeled annotations, to analyze video data and create digital movement biomarkers that are specific to individuals and groups of people. Some examples seek to provide improved methods and systems for creating digital movement biomarkers that can objectively and sensitively measure the impact of drugs on symptoms, facilitate disease diagnosis, and track disease progression, particularly in the context of rare diseases and movement disorders.

In some examples, a model is trained automatically without the need for human annotation. SSL can improve upon human annotated machine learning models by adding temporal context to the video. Temporal context refers in some examples to the information obtained from the sequence of frames in a video. Understanding the natural progression of body key points over time can improve the accuracy of key point tracking.

Some examples leverage SSL to identify or detect objects. SSL can automatically classify objects which provides context to the image. A person sitting on the floor will have different movement than one sitting in a chair. A person walking with the aid of a walker has different movement characteristics than someone walking unassisted. SSL tracks the body movement accurately and recognizes the object in the video which gives it greater value. This context can be especially important for longitudinal analysis. If a subject with a high degree of movement is monitored sitting unassisted on a chair and then later monitored strapped into a wheelchair, the context-less data may show the subject has improved when in fact the subject's condition has declined. The ability of some disclosed SSL examples to generate context of a video can provide important clues, for example the subject is strapped into a wheelchair, such that the resulting data then has greater meaning.

But providing additional context can itself present challenges. For example, data and digital assets derived from key point tracking can include skeletal videos, key point location data, charts and a heat map image summarizing all key point movement. A major challenge can arise providing a research team with contextual data. Because such a study can fall under an Institutional Review Board (IRB) approved protocol in which the subject's personal health information (PHI) is protected, the researchers are not able to view the subject videos. Therefore the movement data derived from the videos can lack context.

In many videos, the subject under analysis may appear to be unsupported when in fact this is not the case. For example, a child or infant subject may be supported by an adult, for example as shown in FIG. 1A. In FIG. 1B, the video has been processed to add key point tracking, but some PHI remains visible. For example, even though the faces of the child subject and adult supporter have been obscured, their bodies are still visible. In FIG. 1C, the adult has been manually masked from the video during further processing so that only the subject body key points are tracked. The researchers therefore only have access to the processed and masked videos which do not provide the context of the adult supporting the child. The subject appears to be an unsupported upright walker and the true situation or context (i.e., the fact of the adult supporter) remains undetected by a conventional pose estimation algorithm. The researchers are left to assume the subject is walking unsupported. Similarly, the subject may be supported by a Zimmer-frame type walker, for example as shown in the video of FIG. 2A. The video data is processed to add key point tracking as shown in FIG. 2B, and is then further processed to remove all PHI as shown in FIG. 2C. This view leaves the researchers again to assume incorrectly that the subject is moving in an unsupported manner.

In relation to rare diseases, subjective outcome measures can be particularly challenging. They lack sensitivity and are prone to human error. Rare diseases, by definition, affect a small number of individuals, which makes conducting clinical research and developing appropriate outcome measures more challenging. Because current outcome measures sometimes fall short, drug developers cannot meet the FDA requirements to prove the medication is efficacious. Outcome measures provided by examples disclosed herein can detect and document small changes objectively and with sensitivity that enable a greater chance for a given medication to get to market. Measures that can be administered at home, for example, without requiring an expert present can make tracking a natural history of the disease more feasible and convenient for patients and caregivers.

Rare genetic disorder symptoms present themselves differently with each person. Many movement disorder symptoms are so nuanced that experts cannot agree on which symptoms they are exhibiting (ataxia, chorea etc.). Some examples herein include a machine learning model that can track elements of patient's genetic fingerprint over time and as it changes with medication. Because the movement biomarker spans all disorders, correlations may be made that between disorders that may have no obvious correlation. For example, fenfluramine, which has been proven effective for managing seizures in Draven Syndrome, is now being researched for effectiveness in FOXG1 syndrome.

Some examples can thus provide a digital movement biomarker specific to an individual and groups of people. This biomarker can be used to measure a drug's impact on symptoms for individuals and disease populations. Identified patient groups with similar digital movement biomarker phenotypes, but no clear commonalities, can be candidates for a common medication.

In some present examples, errant key point detection can be corrected, or excluded as invalid data. In a study to detect Cow Milk Protein Allergy (CMPA) for example, babies experiencing CMPA were identified to move very distinctly, but not in a easily definable way. Errant key points were sometimes generated accordingly by a conventional movement algorithm, for example as shown in FIG. 3B in a series of video frames running from FIG. 3A through FIG. 3C. In FIG. 3B, the subject's left toe appears to be away from the baby potentially indicating a false or erroneous extension of the left leg as part of an apparent movement disorder. In the video frames of FIG. 3A and FIG. 3C the left toe was tracked correctly. Despite the tracking issues, SSL examples of the present disclosure were able to predict the likelihood a baby is experiencing CMPA with a high level of accuracy, around 78%. This was completely independent of any additional inputs such as age or medical history. Kinematic insights included a detection that a CMPA baby's arm angle and velocity are higher than in non-CMPA (healthy) babies. The SLL examples included a baby pose detection model that tracked baby body key point movements and produced kinematic key point data that distilled movement into quantifiable metrics. The kinematic data measured key point and joint factors including positioning, velocity, acceleration, and angles.

Some SSL digital movement biomarker examples utilize temporal context and object detection to improve the accuracy of body key point tracking and to provide meaningful context to the movements captured in video data. For example, no medication has yet been approved that addresses autistic stimming. The improved diagnostic capability enabled by present examples allows for the objective measurement of drug impacts on symptoms and the monitoring of disease progression with greater sensitivity and reduced human error.

Some SSL examples help to identify specific disease characteristics which can include a stable body, hand stimming (repetitive or unusual movements) and feet angles. An objective outcome measure is generated that quantifies specific movement traits over time objectively validating a therapeutic response to treatment. Some subjects having sensory processing neurological disorders can exhibit certain autistic-related stimming movements in common, or the same repetitive, sensory-seeking behaviors. These repetitive movements form the basis of a potential biomarker in some examples that can track repetitive body movement caused by stimming to produce a meaningful outcome measure. Some SSL examples are capable of classifying tracked elements into biomarker profiles, which represent symptoms with numerical values, allowing for comparison and tracking over time. This facilitates the diagnosis of diseases, determination of symptom phenotypes, and measurements of disease severity.

Some examples further includes a compliance mechanism to ensure that video data meets specific quality and contextual criteria, enabling the collection of high-quality data that is meaningful and trustworthy. Kinematic data is extracted from the pose estimation data, providing objective measures of movement characteristics such as volume, velocity, variability, symmetry, and severity.

The present disclosure thus seeks to provide significant advancements in the field of digital health, offering a more objective, sensitive, and error-resistant method for measuring the impact of treatments and understanding disease progression, with particular applicability to rare diseases and movement disorders.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

To easily identify the discussion of any particular element or act, the most significant digit or digits in a reference number refer to the figure number in which that element is first introduced.

DETAILED DESCRIPTION

Figure 1C:
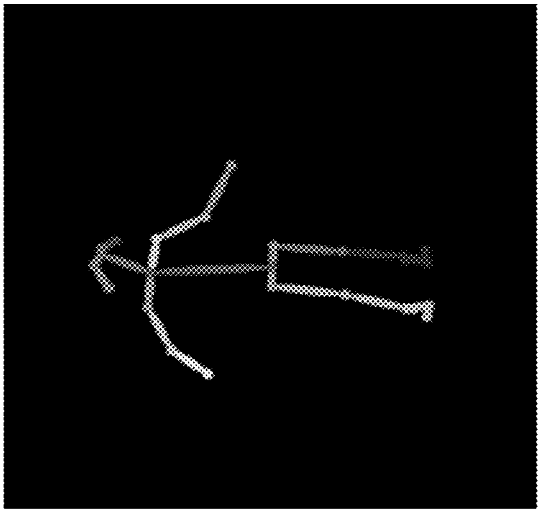
FIG. 1C depicts a video frame after further processing to mask the adult, focusing solely on the subject's body key points for tracking.
Figure 1B:
FIG. 1B shows a processed video frame with key point tracking added, while some personal health information (PHI) remains visible.
Figure 1A:
FIG. 1A illustrates a subject being supported by an adult, demonstrating the initial capture of movement data for analysis.
Figure 2C:
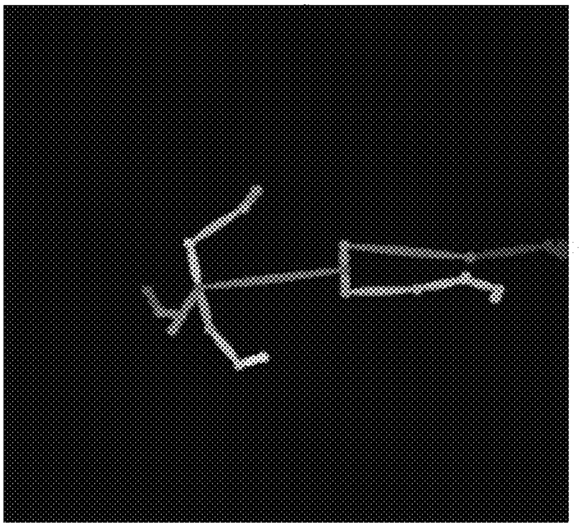
FIG. 2C shows a video frame after processing to remove all PHI, leaving only a subject's movements for analysis.
Figure 2B:
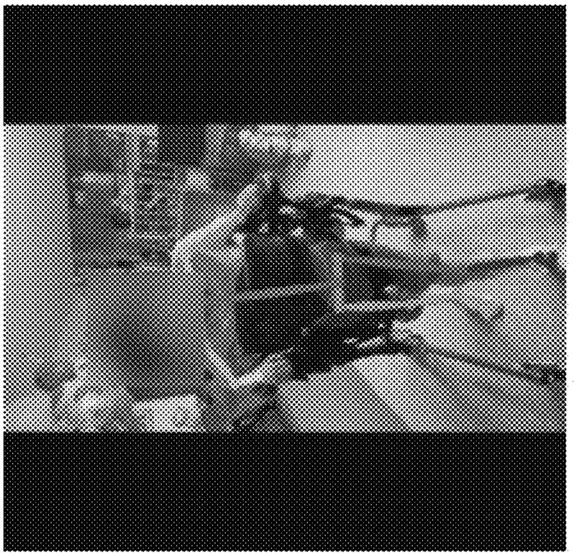
FIG. 2B represents a video frame with added key point tracking, highlighting a subject's movements with a walker.
Figure 2A:
FIG. 2A displays a subject supported by a Zimmer-frame type walker, as captured in the original video data.
Figure 3C:
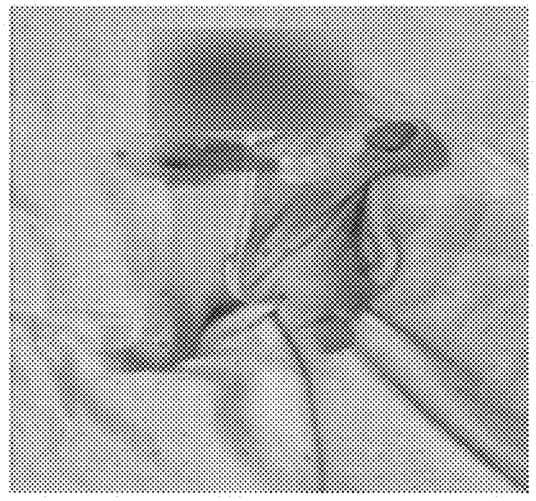
FIG. 3C shows a video frame where the key point tracking has been corrected, accurately representing the subject's movement.
Figure 3B:
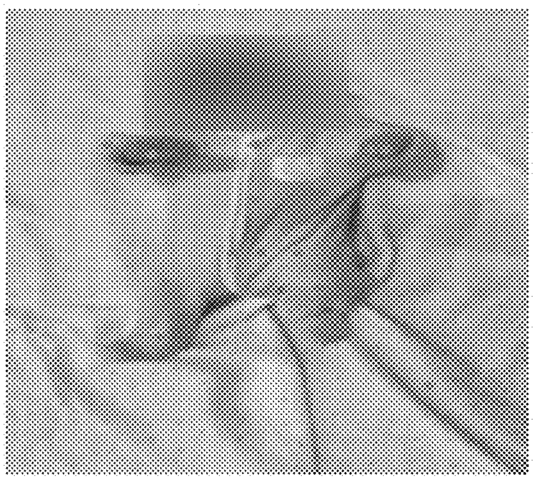
FIG. 3B illustrates a video frame with errant key point detection, where the left toe appears away from a baby's body.
Figure 3A:
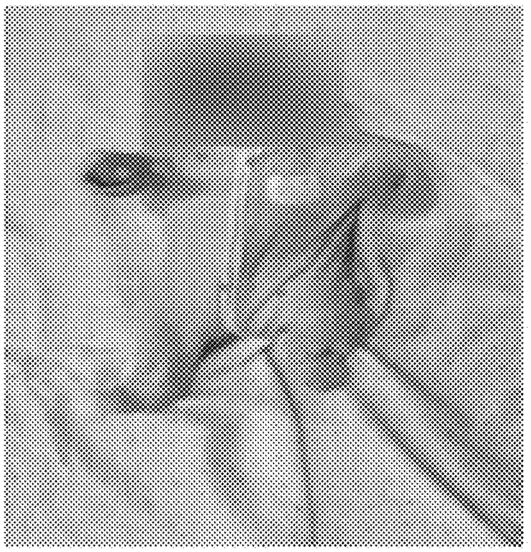
FIG. 3A depicts a video frame from a video sequence with correct key point tracking of a subject's movement.

In some examples, a digital SSL movement biomarker system employs a machine learning methodology and data processing pipeline to create digital movement biomarker profiles, utilizing self-supervised learning (SSL) techniques to analyze video data of subjects. The SSL framework is a subset of unsupervised learning where the model is trained to understand and predict parts of the input data by creating pretext tasks, such as predicting subsequent frames in a video sequence. This training is conducted on a substantial dataset of unlabeled video data, allowing the model to learn patterns and features without the need for explicit annotations. The model's ability to capture temporal context by recognizing the sequence of frames is crucial for accurately tracking the progression of body movements over time.

Once the SSL model has been trained on the unlabeled data, it undergoes a downstreaming process. During this phase, the model is fine-tuned with a smaller, labeled dataset to enhance its accuracy for specific tasks, including pose estimation and object detection. This two-tiered training approach allows the model to develop a robust understanding of the data before applying it to precise tasks, significantly reducing the need for extensive labeled datasets from the outset.

The data processing pipeline begins with the capture of video data, ensuring that the subject's entire body is visible for accurate movement tracking. Videos are subjected to compliance checks against predefined criteria, such as proper lighting and camera stability, to ensure data quality. Non-compliant videos are flagged for recapture or excluded from the analysis.

The SSL model is then applied to the compliant video data to perform pose estimation, tracking body key points such as joints and limbs. Concurrently, the model detects objects within the video that interact with the subject, such as chairs or walkers, providing essential context to the movements being analyzed. From this data, kinematic features such as distance, velocity, acceleration, symmetry, and repetition are extracted. These features form the basis of objective measures of movement characteristics, which are critical for assessing the subject's condition.

The extracted kinematic data is then analyzed to quantify symptoms, resulting in the creation of a digital movement biomarker profile for the subject. This profile includes numerical values that represent the severity and type of symptoms, enabling tracking over time and comparison across different assessments. The model classifies the digital movement biomarker based on the entirety of the content, leveraging both kinematic information and image context to provide a comprehensive representation of the subject's health condition.

For longitudinal analysis, the system can compare biomarker profiles over time to assess disease progression or the impact of treatments. Digital movement biomarker profiles are stored in a secure database, facilitating easy retrieval for further analysis or comparison. Additionally, the system generates visualizations such as heat maps and charts to summarize key point movements, aiding clinicians in the interpretation of the data.

This methodology and pipeline represent an objective approach to creating digital movement biomarker profiles that are not only accurate and sensitive but also tailored to the unique characteristics of individual subjects. The use of SSL addresses the challenges associated with manual annotation and leverages the vast amounts of available unlabeled data, which is particularly beneficial in the healthcare domain where labeled data can be scarce and costly to obtain.

Figure 4:
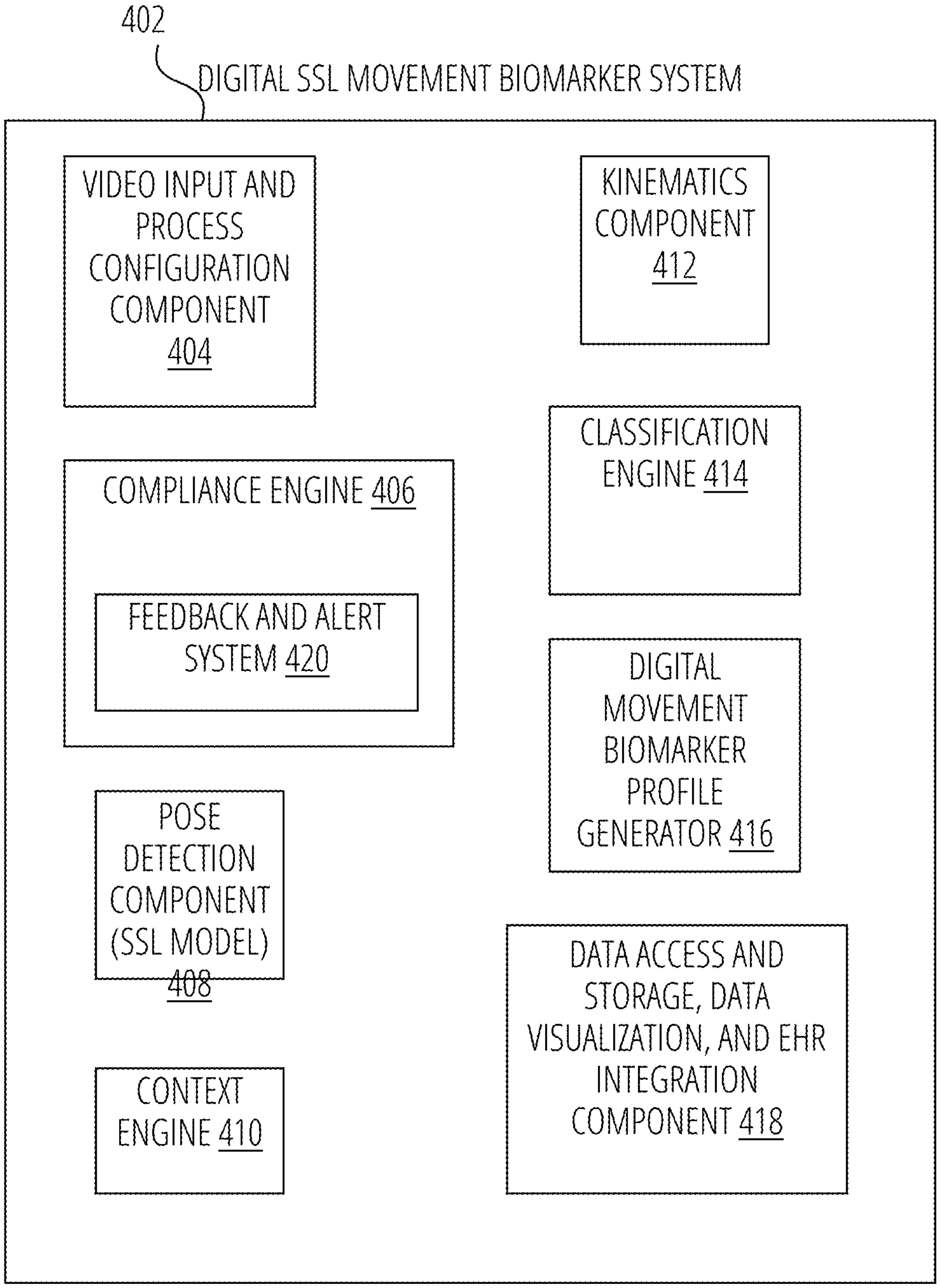
FIG. 4 provides an overview of an example digital SSL movement biomarker system with various components for data processing and analysis.

FIG. 4 illustrates various components within a digital SSL movement biomarker system 402 that perform a series of operations to identify, integrate, and display digital SSL movement biomarkers. These and further example operations performed by the components of the digital SSL movement biomarker system 402 are also described below with reference to FIG. 5.

In FIG. 4, a video input and process configuration component 404 is responsible for receiving a raw video file that may include optional inputs such as the date of birth, genetic profile, and video orientation of the subject. A compliance engine 406 performs an initial check to ensure that the video meets specific requirements for analysis. This includes ensuring all body parts are within the video frame, the camera is stable, the video duration is sufficient, the lighting conditions are adequate, and the clothing of the subject does not blend with the background. Once the video passes the compliance check, a pose detection component (SSL model) 408 component, powered by a self-supervised learning (SSL) model, analyzes the video to detect body parts and perform pose estimation. This component is of note for identifying the positions and movements of various body key points.

A context engine 410 adds a layer of understanding by providing temporal context and object detection. The context engine 410 is responsible for recognizing objects in the video, such as chairs or walkers, which provides context to the subject's movements. This component ensures that the movement data is interpreted correctly, considering the environment and support devices used by the subject. A kinematics component 412 measures the kinematics of the detected movements, such as distance, velocity, acceleration, symmetry, and repetition. It quantifies the movement characteristics, providing detailed data on how the subject is moving. A classification engine 414 takes the kinematic data and, using the trained SSL model, classifies the movements. It understands the temporal, spatial, and contextual elements of the video to create a meaningful representation of the content. This component may classify the digital movement biomarker based on disease diagnosis, symptom phenotypes, or severity of disease.

Based on the classification results, a digital movement biomarker profile generator 416 generates digital movement biomarker profiles that represent the movement symptoms of the subject. Each symptom is quantified and represented in the profile, which can be used for diagnostic purposes or to track the progression of a disorder over time. Finally, by a data access and storage, data visualization, and EHR integration component 418, the digital movement biomarker profiles are stored securely and made accessible to authorized users, such as healthcare providers or researchers. This component ensures that the data can be retrieved and used for further analysis, visualized as discussed further below, integrated with electronic health records, to assist with diagnostic support and in clinical decision-making.

Each of these components works in concert to process and analyze the video data, extract meaningful movement biomarkers, and provide actionable insights for clinicians. The system's modular design allows for each step of the process to be handled by specialized components, ensuring accuracy and efficiency in the generation of digital movement biomarker profiles.

In some examples, a "component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner.

In examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations.

A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. A decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein.

Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors.

Similarly, the methods described herein may be at least partially processor-implemented, with a particular processor or processors being an example of hardware. For example, at least some of the operations of methods described herein may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In some examples, the processors or processor-implemented components may be distributed across a number of geographic locations.

Figure 5:
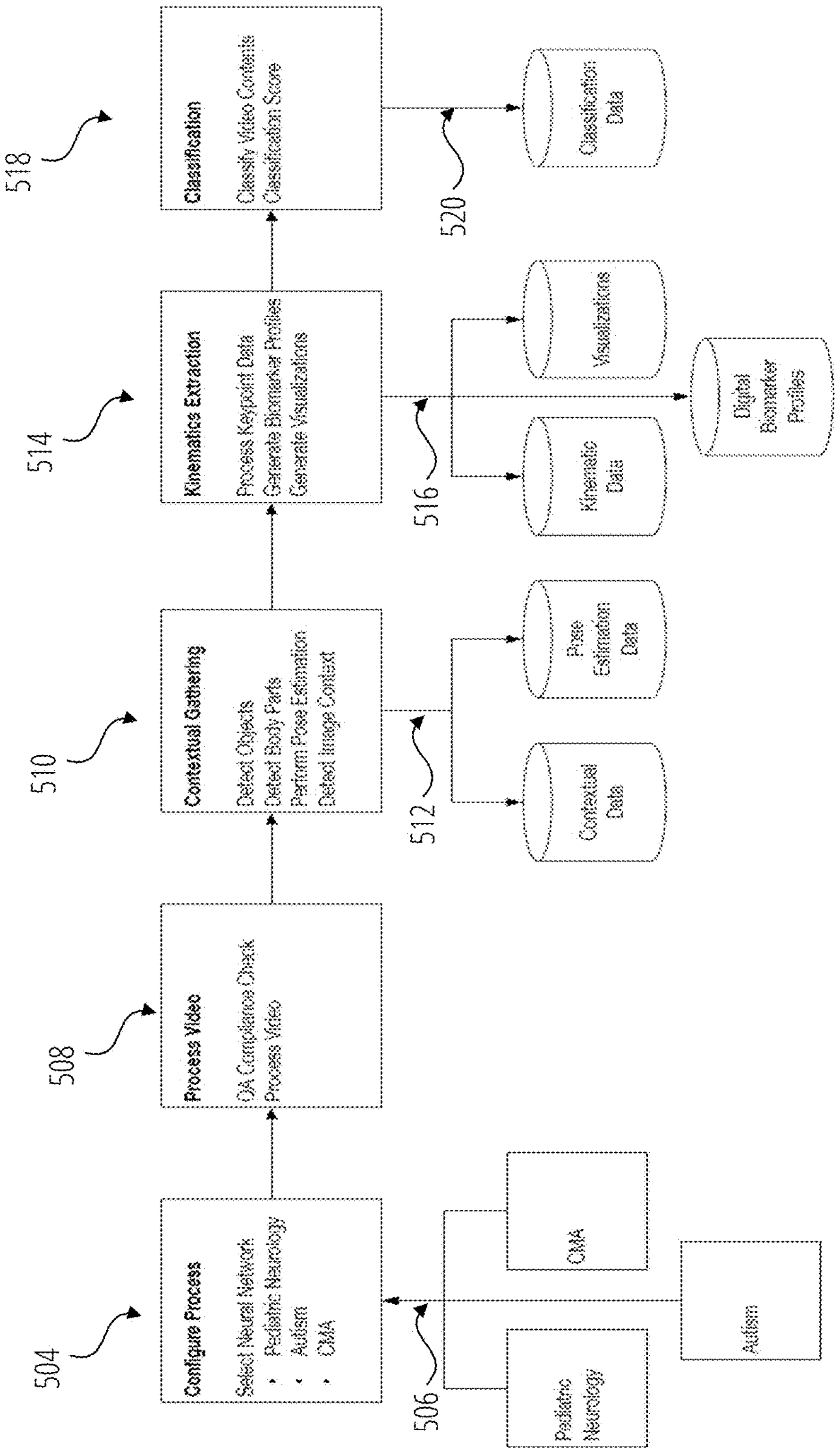
FIG. 5 provides some aspects of an example process configuration and data collection and processing steps.

With reference to FIG. 5, in some examples, the video input and process configuration component 404 performs a process configuration 504. This may include a selection of a neural network for analysis, or aspects of an associated disease for study, such as pediatric neurology, autism, or CMA. Other diseases are possible. The video input and process configuration component 404 may perform data collection 506 relating to a selected neural network, or one or more aspects relating to a disease. Some or all of the data collected may include unlabeled data. The data collected may include videos of one or more subjects affected by a given disease.

In some examples, the compliance engine 406 performs video processing 508. In some examples, this component checks the video for compliance with predefined criteria. If the video is non-compliant, it is directed to a feedback and alert system 420 that notifies a user or researcher to correct the issues.

In some examples, the context engine 410 adds context to the pose data by detecting objects and providing temporal context. In some examples, the context engine 410 performs context gathering 510. This may include detection of objects or body parts in an analyzed video, or detecting an image context. In some examples, the context engine 410 works in conjunction with the pose detection component (SSL model) 408 to perform pose estimation. The pose detection component (SSL model) 408 processes compliant videos to detect body parts and estimate poses using SSL techniques. The context engine 410 and pose detection component (SSL model) 408 may perform context data generation 512. The context data generation 512 may include context data and pose estimation data. This contextual data may be gathered, accessed, and stored by the data access and storage, data visualization, and EHR integration component 418.

In some examples, the kinematics component 412 performs kinematics extraction 514. This component calculates kinematic data such as distance, velocity, and acceleration of body movements or detected body parts and/or key points. In some examples, the kinematics component 412 processes key point data, generates biomarker profiles, and generates biomarker profile visualizations. Example data visualizations are discussed further below. Data generated or accessed by the kinematics component 412 may be collected in kinematic data collection and access 516 operations. The collected or accessed data may include kinematic data, visualization data, and digital biomarker profile data.

In some examples, the classification engine 414 performs classification 518. The classification engine 414 classifies the movement data based on the kinematic and contextual analysis and generates classification data 520. In some examples, the classification engine 414 classifies video contents and assigns a classification score. In some examples, the classification data 520 generated by the classification engine 414 is transmitted to the digital movement biomarker profile generator 416 that generates a digital biomarker profile from the classified data. In some examples, the data access and storage, data visualization, and EHR integration component 418 stores the generated profiles and makes them accessible for further use.

In some examples, the self-supervised learning (SSL) approach removes the need for manual annotation of body key points by leveraging patterns from unlabeled data, diverging from the conventional supervised method. During training, the model is exposed to input data and applies transformations or perturbations to generate modified data versions. Its goal is to predict the original, unmodified data based on these altered versions. This process allows the model to grasp significant patterns and latent representations within the data. Once the model is trained, a small, labeled dataset is used to retrain the model, enabling it to accurately classify data into their respective classes. Unlike the supervised approach, which requires a large, labeled dataset from the start, this method significantly reduces the labeling burden. This retraining process is referred to as downstreaming, and it enables the trained self-supervised model to be applied to various tasks, including body part detection, pose estimation, and image context detection. In the healthcare field, acquiring a substantial annotated dataset is particularly challenging compared to other domains due to the expertise required for annotation. Moreover, human annotation is prone to imprecision and inconsistency. Therefore, the self-supervised approach can provide a more appropriate or convenient solution for healthcare applications, addressing the limitations associated with human annotation and enabling effective utilization of available unlabeled data.

Figure 6C:
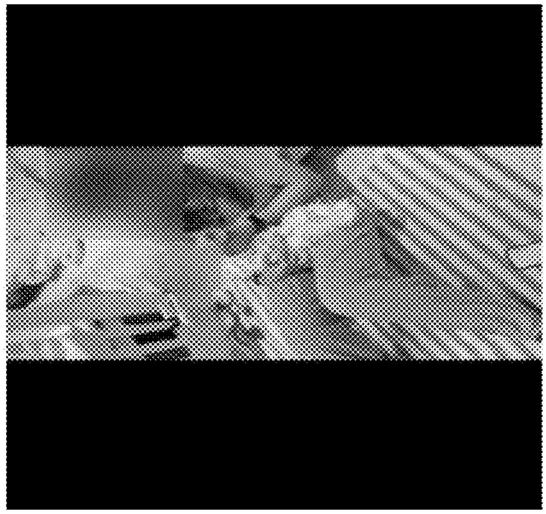
FIG. 6C illustrates a non-compliant video with the subject being held by an adult, affecting the movement data.
Figure 6B:
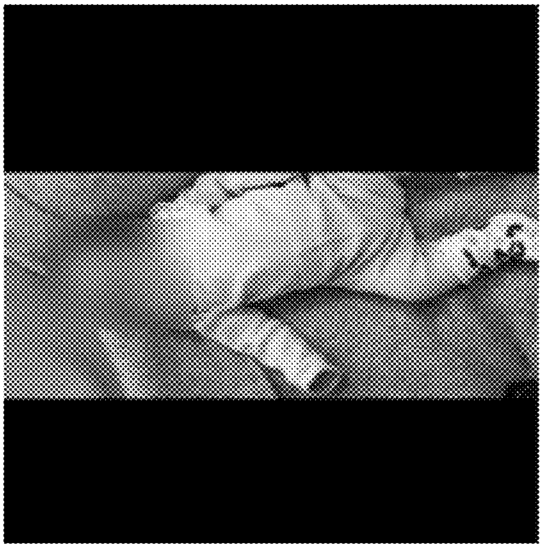
FIG. 6B shows a non-compliant video where the subject's arm and leg are out of the frame.
Figure 6A:
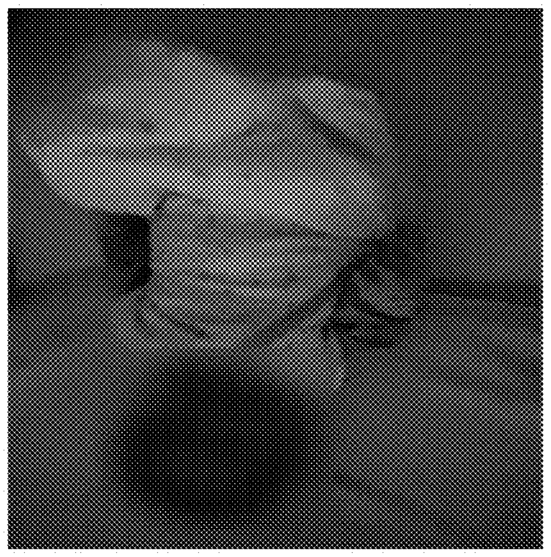
FIG. 6A illustrates a frame from a non-compliant video due to poor subject lighting conditions.

With reference to FIG. 6A, FIG. 6B, and FIG. 6C6, in some examples certain requirements, parameters, or errors which are not obvious to those recording a subject's movements in a video can be identified. This identification can help to extract maximum diagnostic value from the video. Non-medical parents or caregivers especially may benefit from direct feedback on non-compliant videos. For example, in FIG. 6A, the subject lighting is too dark. In FIG. 6B, the subject's arm and leg are out of the video frame. In FIG. 6C, the subject is being held by an adult. Understanding a video's context and an ability to track body key points accurately (in correct context) enables SSL models to provide direct and specific feedback to the recorder. Because some examples are SSL-driven, pre-determined errors or instances of non-compliance are not necessarily required. In some examples, non-compliance issues are automatically categorized and transmitted to the parent or caregiver. In some examples, these non-compliance messages are generated by the compliance engine 406 and the feedback and alert system 420. Specific compliance requirements may include one or more of: all body parts in video at all times, stability (camera not moving excessively), video duration, a lighting condition, a number of people in the video, and/or subject clothing that does not blend with a background.

Figure 7:
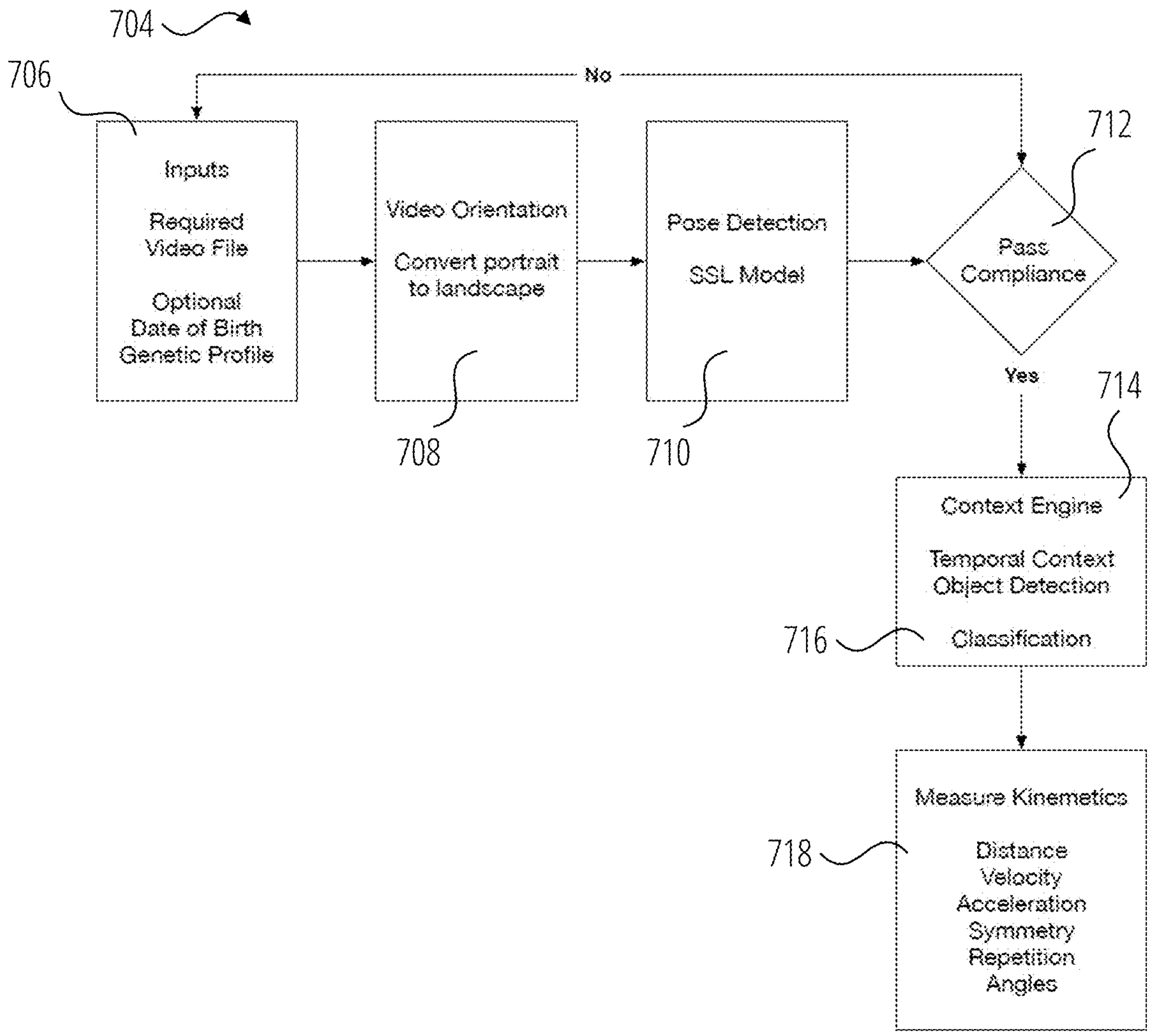
FIG. 7 outlines a process flow for analyzing video data using a self-supervised learning (SSL) model to extract kinematic information, for example.
Figure 8A:
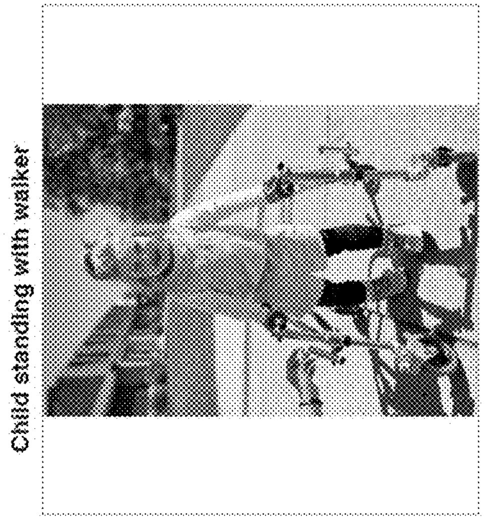
FIG. 8A through FIG. 8I depict various scenarios and configurations of subjects and their movements, demonstrating the system's capability to capture and analyze diverse movement patterns.
Figure 8B:
Figure 8C:
Figure 8D:
Figure 8E:
Figure 8F:
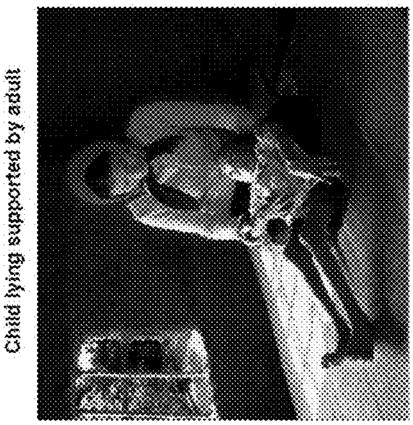
Figure 8G:
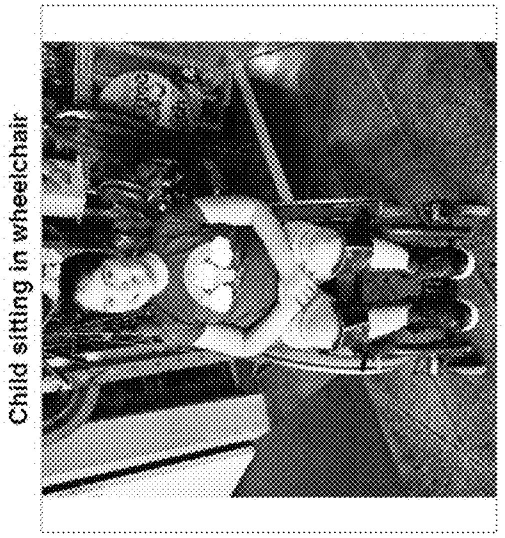
Figure 8H:
Figure 8I:
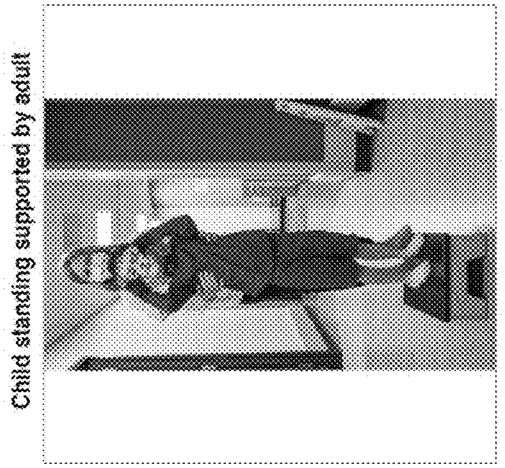

Reference is now made to the example process flow 704 shown in FIG. 7. The process flow 704 outlines a simplified process for analyzing video data to extract kinematic information using a self-supervised learning (SSL) model. At inputs operation 706, the video input and process configuration component 404 receives a video file of movements of a subject as input, with optional additional data such as the date of birth and genetic profile of the subject. At video orientation operation 708, the video input and process configuration component 404 may need to convert the video orientation from portrait to landscape for consistent analysis. At pose detection operation 710, the pose detection component (SSL model) 408 detects the pose (or one or more poses, or movements) of the subject within the video. At compliance check operation 712, the compliance engine 406 runs a compliance check to ensure the video meets the necessary criteria for analysis. If not, the inputs operation 706 through pose detection operation 710 may be run again. If the compliance checks are passed, the process flow 704 proceeds to context processing operation 714.

In context processing operation 714, the context engine 410 provides temporal context and object detection, which can be of significance for properly understanding the movements of the subject within the video, for at least the reasons mentioned above. In classification operation 716, the classification engine 414 classifies the video contents based on movement patterns and any context detected.

In kinematics operation 718, the kinematics component 412 determines various kinematic aspects such as distance, velocity, acceleration, symmetry, repetition, and angles of the movements detected in the video. Some example kinematics components 412 compute kinematic information such as velocity, acceleration, angular velocity, and angular acceleration for each body part and joint. This added level of detail furnishes supporting evidence for the final classification outcome and enhances an understanding of the model's results. Moreover, the availability of supporting data can be essential for regulatory compliance, such as the FDA, and documentation of the performance of the subject under analysis, and the SSL model used for diagnostic support.

The various components of some examples are specially configured or designed to handle specific aspects of the video analysis process, from input and compliance to pose detection, context analysis, kinematics measurement, and classification. These components work together to generate a comprehensive digital movement biomarker profile based on the video data. In some examples, a trained SSL model can extract meaningful features from videos. Understanding the temporal, spatial and contextual elements of the video enable a more meaningful representation of the video's content. The SSL model can classify the digital movement biomarker based on the entirety of the content. By leveraging all the existing data, including kinematic information and image context, a distinct classification SSL model will undergo training. This SSL model can be utilized for various classifications, such as disease diagnosis, determination of disease symptom phenotypes, or measurements of disease severity.

Every individual is unique, with varying responses to medication, including its effects on symptoms, side effects, and efficacy over time. A digital SSL movement biomarker (or "biomarker" herein) can serve as a valuable tool to track symptoms both at an individual and group level. Similar to a symptom fingerprint, the biomarker captures distinct patterns. Unlike a physical fingerprint, groups of individuals or entire patient populations can share the same digital fingerprint or biomarker. In some examples, the identification and development of a digital movement biomarker relies entirely on machine learning techniques. By harnessing cutting-edge machine learning algorithms and artificial intelligence, the makeup and significance of the biomarker can be determined.

In some examples, a biomarker accurately and sensitively tracks the most influential elements of body movement. In some examples, these tracked elements are classified by a neural network, specifically targeting the characteristics commonly associated with the disorder. To ensure the measured data is meaningful and trustworthy, temporal and spatial video information is combined with feature extraction. This integration provides context for the measured data which can be important for establishing trust. Knowing precisely what is being tracked forms a critical component of comparison. It allows for fair comparisons by ensuring that the characteristics of a subject's behavior over time are tracked, without introducing unrelated elements. Clean and meaningful data can be essential for reliable analysis. Some example scenarios from which clean and meaningful data was derived by a digital SSL movement biomarker system 402 of the present disclosure are shown in FIG. 8A through FIG. 8I.

Some examples of a digital SSL movement biomarker system 402 quantify movement characteristics, assigning each a significance factor on a scale from zero, indicating normalcy, to 100, denoting severe impact. This scale contemplates the extreme range of each characteristic. The data for these assessments are derived from both self-supervised learning (SSL) generated body parts and body pose estimation key points. Objective measures of movement include volume, physical distance, time, movement velocity, movement variability, movement symmetry, and movement acceleration. Additionally, the system evaluates repetitive movements such as body rocking, hand twirling, "stimming", speech patterns, and tremors.

Severity of movement is gauged through joint angles—including the wrist, ankle, elbow, and shoulder—with metrics such as mean angles, standard deviation, mean angular velocity, cross-correlation, and entropy. Further analysis extends to body key point velocity and acceleration, joint angle velocity and acceleration, as well as overall stance, body position, head/neck position, postural information, absolute position, and arm swing. Gait analysis is conducted by measuring step distance, foot angle, speed, toe-off angle, and cadence. Longitudinal analysis tracks these metrics over time against a baseline to establish natural history and standard units across disorders.

The system recognizes that factors may vary between disorders and individuals, yet it can identify shared traits such as stimming behaviors and joint angles. This capability allows for the comparison of subject traits across and within disorders and the detection of disorders based on these traits. The SSL-generated body parts correlate with body key points, providing insights that may be more significant than key points alone, such as in the analysis of a foot comprising toe(s), heel, and ankle key points.

Figure 9:
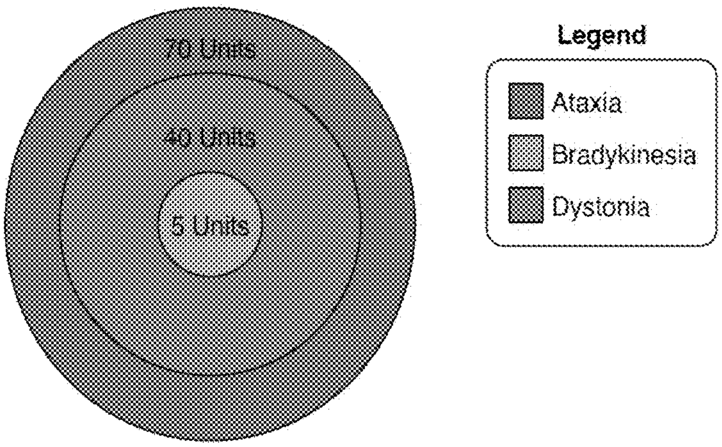
FIG. 9 shows an example data visualization output, displaying a digital movement biomarker profile in a roundel-type configuration.

Inputs to the system include genetic profiles, date of birth or age, video data, and clinical data when available. SSL digital movement biomarker profiles encapsulate all classified movement symptoms, and each profile can be represented by a numerical unit volume of movement. An example data visualization output is shown in FIG. 9. The output is visually and conveniently displayed in a roundel-type configuration and provides a profile value as "Profile Value=70 units symptom A+40 units symptom B+5 units symptom C". Symptoms A, B, and C may, for example, be associated respectively with ataxia, bradykinesia, and dystonia. The respective unit values of 70, 40, and 5 can serve, in some examples, as a blind indicator of a symptom's severity, independent of the disorder, thus enabling the association of symptom similarities across disorders without bias. This convenient, de-siloed, and self-learned approach to symptom measurement addresses challenges in rare disease therapy development. Examples can facilitate the rapid and accurate understanding and validation of new FDA-approved outcome measures, surpassing the capabilities of current methodologies.

Figure 10:
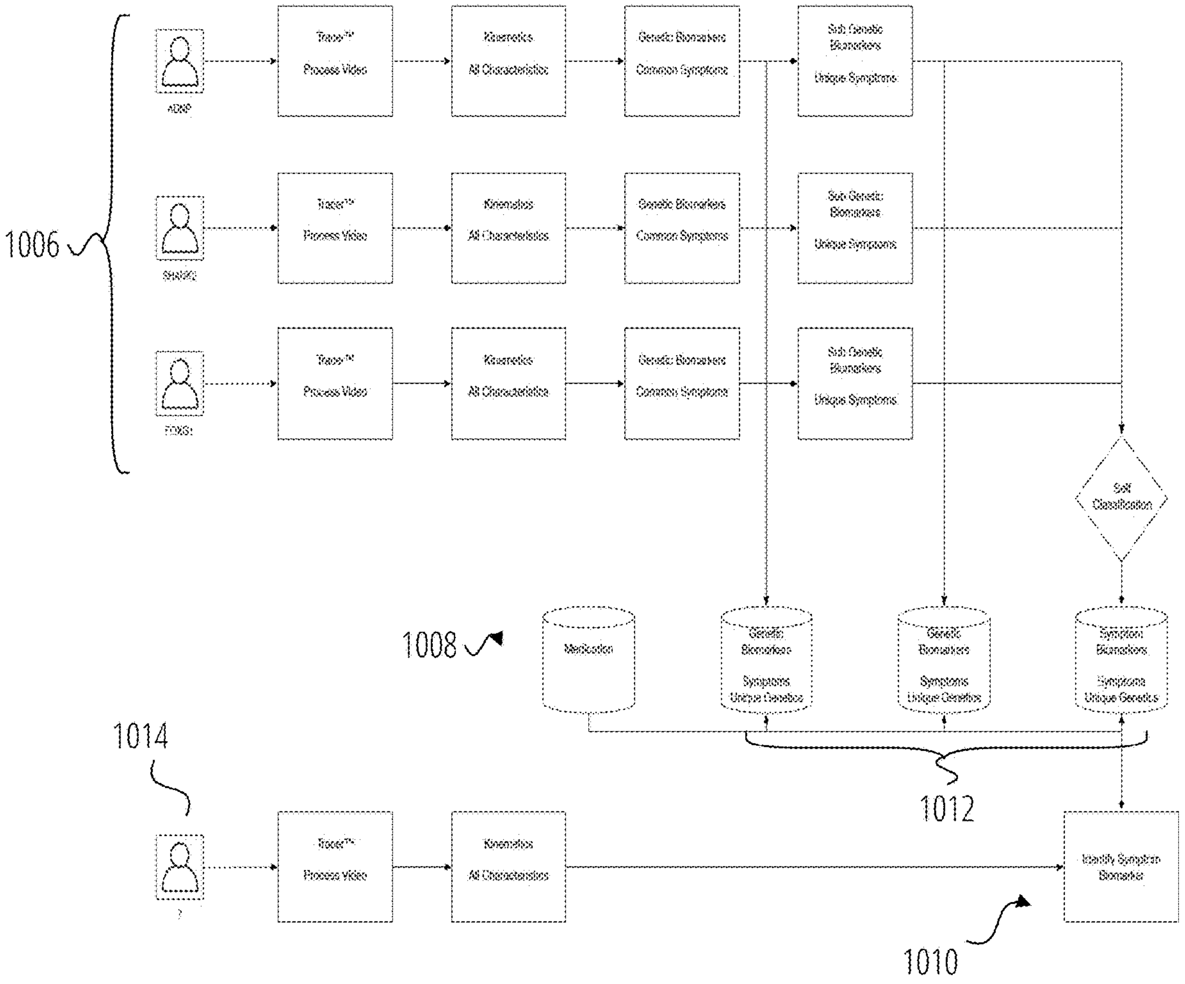
FIG. 10 illustrates a segmentation process of movement biomarkers, highlighting the analysis of genetic disorders and the generation of biomarker profiles.
Figure 11:
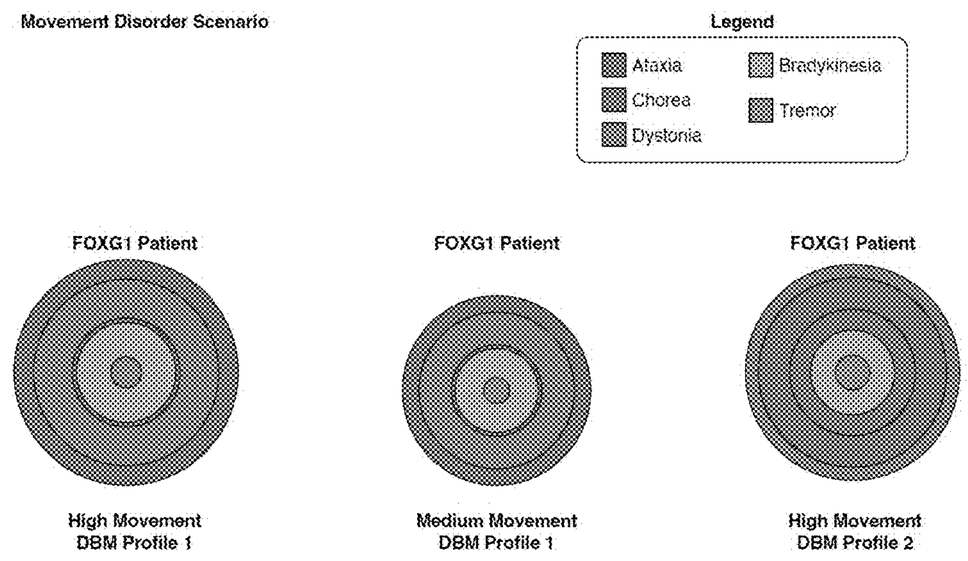
FIG. 11 through FIG. 14 provide examples of data visualization techniques used to present digital movement biomarker profiles, including roundels, heat maps, skeletal videos, and kinematic charts.
Figure 12:
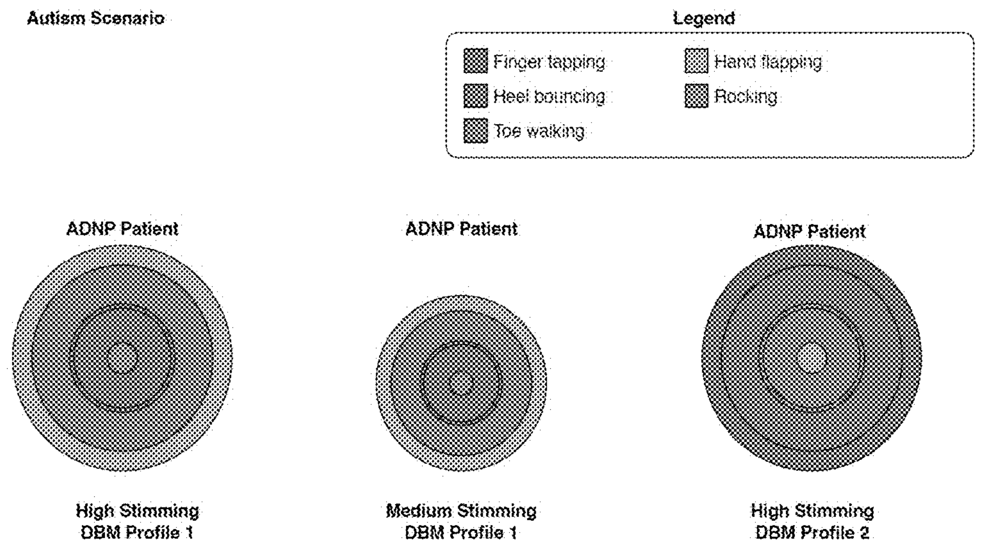
Figure 13:
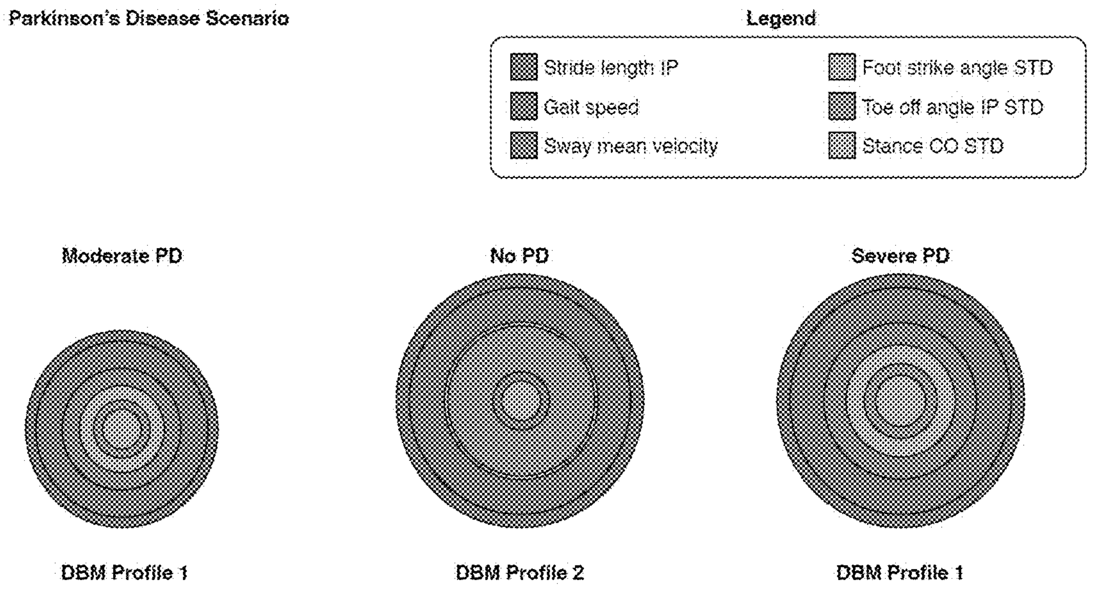
Figure 14:
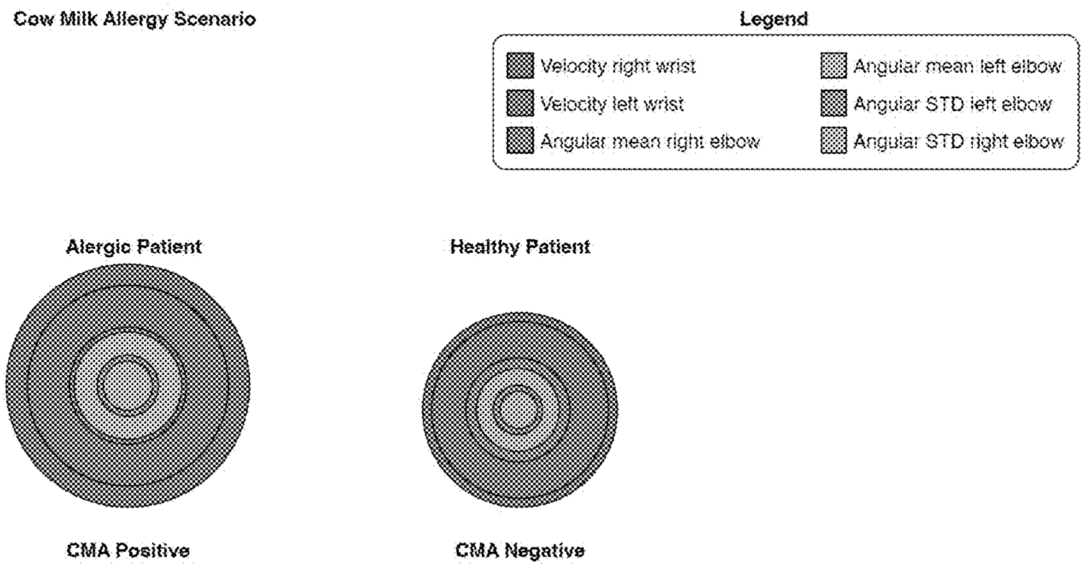

With reference to FIG. 10, some examples of a digital SSL movement biomarker system 402 include digital SSL movement biomarker segmentation techniques. Consolidation of biomarker data within disorder groups can add meaningful granularity to the understanding of movement symptoms and how they change over time. Some symptoms are common to all in certain disease groups and some are more random.

Certain genetic disorders share a symptom but express the symptom uniquely per disorder. Some example disorders in this regard include those that express autistic behaviors. A subject within one disorder may, for example, exhibit stimming behaviors such as rocking back and forth in a consistent manner, while a second disorder may exhibit a rocking type of stimming in a different way. In some instances, disclosed examples can identify a first subject suffering from disorder A from a group of second-disorder B subjects as the only person stimming in a different manner. Additionally, certain secondary symptoms or mutation types (missense, deletion, etc.) are more likely to benefit from certain therapies than others. Understanding a medication's effect on secondary symptoms (not the ones necessarily targeted) can provide evidence for additional opportunities within and outside of the target genetic mutation.

In some examples, a digital movement biomarker identified by the techniques disclosed herein may identify a common characteristic shared between two people suffering from the same or different diseases. A person with an unknown diagnosis may be diagnosed with a given disorder based on a common biomarker profile. In some cases, this enables an early diagnosis and has the potential to significantly reduce the time to make a diagnosis using conventional techniques. For examples, a Parkinson's disease diagnosis can take an average of 2.75 years to diagnose, while an analysis yielding movement biomarkers identifiable by present examples may enable a diagnosis ten years earlier.

FIG. 10 illustrates a segmentation process of movement biomarkers as a further analytical capability of an example digital SSL movement biomarker system 402. This process can facilitate an understanding of the complex interplay of genetic and symptomatic expressions across various disorders. The illustrated segmentation is depicted through the representation of three distinct genetic disorders: ADNP, SHANK2, and FOXG1. Each disorder can be analyzed to identify unique symptoms and sub-genetic biomarkers that contribute to an overall phenotype of the disorder. The analysis of each disorder is, in some examples, conducted as described further above including, for example, operations such as video processing, kinematic extraction, genetic digital SSL movement biomarker generation (based on common symptoms) and sub genetic digital SSL movement biomarker generation (based on unique symptoms). In some examples, the analysis of each disorder is conducted as part of a training 1006 of a digital SSL movement biomarker system 402, or one or more SSL models.

The biomarker segmentation process can in some examples capture nuanced expressions of each disorder, recognizing that while certain symptoms may be shared across disorders (for example, common symptoms), their manifestation can be unique to each genetic condition (for example, unique symptoms). For instance, individuals with ADNP syndrome may exhibit a set of symptoms and biomarkers that, while potentially overlapping with those associated with SHANK2 or FOXG1, will also include distinct traits specific to ADNP.

Furthermore, the segmentation process allows for the comparison of traits within a disorder, providing a deeper understanding of the variability and commonality among affected individuals. This comparison can be helpful for establishing tailored therapies 1008 such as tailored personalized treatment plans, medication, and/or for advancing the development of targeted therapies. The process can also facilitate, for example at diagnosis 1010, the detection of disorders based on the presence and combination of certain common and/or unique symptoms or traits, potentially leading to earlier and more accurate diagnoses.

FIG. 10 further illustrates a capability of the digital SSL movement biomarker system 402 to integrate genetic profiles, clinical data, and video analysis to construct a comprehensive biomarker profile 1012. By leveraging the self-supervised learning (SSL) model, the system can process video data obtained, for example, from a subject 1014 to extract movement characteristics, kinematics, and/or SSL movement biomarkers and correlate them with previously-trained body key points, offering insights that may be more revealing than traditional key point analysis alone. The digital SSL movement biomarker system 402 can in some examples thus facilitate and support the diagnosis and treatment of genetic disorders by providing a granular, data-driven view of disease phenotypes.

With reference to FIG. 11-FIG. 14, some examples of a digital SSL movement biomarker system 402 include data visualization capabilities configured to present the digital biomarker profiles to clinicians in an intuitive and informative manner, facilitating the interpretation of complex movement data and aiding in clinical decision-making. The digital SSL movement biomarker system 402 system converts the kinematic and classification data derived from the SSL model into visual formats that highlight key aspects of the subject's movements and symptomatology. These aspects can provide diagnostic support.

Example visualization techniques can include roundel-type format as discussed above, and as shown for example in FIG. 11-FIG. 14. Each roundel has one or more concentric rings as shown indicating or representing a severity of an observed trait, movement, or diagnosed disease based on one or more digital SSL movement biomarkers identified by the digital SSL movement biomarker system 402. The roundels generated by a digital SSL movement biomarker system 402 can include heat maps or zones that provide a visual representation of movement intensity across different body parts. These maps can indicate areas of frequent movement or stability, helping clinicians to quickly identify patterns that may correspond to specific symptoms or disease manifestations.

In some examples, skeletal videos are generated by the digital SSL movement biomarker system 402. By overlaying tracked key points onto an original video, the digital SSL movement biomarker system 402 creates skeletal representations of the subject's movements. This allows clinicians to observe the movement patterns in a simplified form, focusing on the mechanics of the motion without the distraction of the video's background or other non-relevant visual information.

In some examples, the digital SSL movement biomarker system 402 produces various charts and graphs that plot kinematic data over time, such as velocity, acceleration, and joint angles. These visualizations can show changes in movement characteristics, allowing clinicians to track the progression of symptoms or the impact of therapeutic interventions over time.

In some examples, the digital SSL movement biomarker system 402 produces movement profiles. Digital movement biomarker profiles are visualized as composite scores or graphs that combine multiple movement characteristics into a single profile. This profile can be compared against a baseline or across different time points to assess changes in the subject's condition.

In some examples, the digital SSL movement biomarker system 402 provides comparative analysis. The system can display side-by-side comparisons of digital movement biomarker profiles from different subjects or from the same subject at different times. This comparative analysis can help clinicians identify commonalities or differences in movement patterns, which may be indicative of treatment efficacy or disease progression.

Some examples facilitate presentation of digital movement biomarker profiles. For example, a digital SSL movement biomarker system 402 includes a user-friendly interface that allows clinicians to navigate through different visualizations, select specific data points for closer examination, and switch between individual and aggregate data views. Clinicians can customize dashboards to display the most relevant visualizations for their needs, enabling them to focus on the most pertinent information for diagnosis or treatment monitoring. Visualizations include interactive elements, such as the ability to zoom in on specific data points, filter data by various parameters, and hover over elements to display additional details. In some examples, the digital SSL movement biomarker system 402 provides options for clinicians to annotate visualizations with their observations and insights. These annotated visualizations can be included in reports or patient records, ensuring that the clinician's expert interpretation accompanies the raw data.

Notably, in some examples, the digital SSL movement biomarker system 402 can integrate with EHRs to combine visualizations with other patient data, offering a comprehensive view of the patient's health status and facilitating a holistic approach to care. The data visualization capabilities of the digital SSL movement biomarker system 402 can be helpful for translating the complex data generated by the SSL models into actionable insights. By providing clinicians with clear and accessible visual representations of digital biomarker profiles, the system enhances the ability to diagnose diseases, monitor treatment responses, and understand disease progression with greater precision and confidence.

The integration and comparison of digital movement biomarker profiles with patient medical records and lab tests can enhance the clinical applicability of the digital SSL movement biomarker system 402. This process combines quantitative movement analysis with conventional medical data, offering a holistic view of a patient's health status. The following paragraphs describe some examples steps involved in this process.

The integration process begins with data standardization and formatting, ensuring that digital movement biomarker data and medical records are in compatible formats. This step may involve the use of standardized medical coding systems such as ICD-10, LOINC, and SNOMED CT, which help streamline the integration of data. Following this, secure data transfer protocols like HL7 and FHIR are implemented to facilitate the safe movement of digital movement biomarker data into the Electronic Health Record (EHR) system, while maintaining compliance with privacy regulations such as HIPAA or GDPR.

Once the data transfer is complete, the EHR system is updated to accommodate digital movement biomarker data, which may include adding new fields or creating a dedicated section for movement analysis and visualization. Digital movement biomarker profiles are then linked to corresponding patient records using unique identifiers, allowing for the correlation of movement data with the patient's medical history, diagnosis codes, and lab test results.

To enhance the utility of this integrated data, visualization tools are embedded within the EHR interface. These tools enable clinicians to view roundels, heat maps, skeletal videos, and kinematic charts directly within the patient's record, for example as discussed above. Additionally, the EHR system is equipped with comparative analysis tools that allow clinicians to perform longitudinal analyses of digital movement biomarker profiles and compare them against population norms or overlay lab test trends with movement data to uncover potential correlations.

The comparison process involves the temporal alignment of digital movement biomarker data with medical events, treatments, and lab tests to evaluate temporal relationships. Statistical tools are employed to compare movement patterns with clinical outcomes or lab test abnormalities, identifying patterns that may signal treatment effectiveness or disease progression.

A multidisciplinary team, including neurologists, geneticists, and physical therapists, is facilitated to review the integrated data, providing a comprehensive assessment of the patient's condition. This collaborative approach informs treatment planning, enabling adjustments to therapies based on insights from both digital movement biomarker profiles and traditional medical data.

In some examples, patient engagement is a component of this process. Patients are given access to their digital movement biomarker profiles and medical records through patient portals, empowering them to understand the connection between their movement data and overall health. Finally, a continuous monitoring and feedback loop is established, where ongoing patient monitoring with the SSL digital movement biomarker system informs future medical evaluations and lab tests, allowing for the fine-tuning of medical interventions based on integrated data analysis.

Integrating and comparing digital movement biomarker profiles with patient medical records and lab tests not only provides clinicians with a more detailed understanding of a patient's condition but also enhances the precision of diagnoses, personalizes treatment plans, and improves patient outcomes. This integrated approach also supports research by offering a rich dataset for exploring the relationships between movement patterns and various medical conditions.

Figure 15:
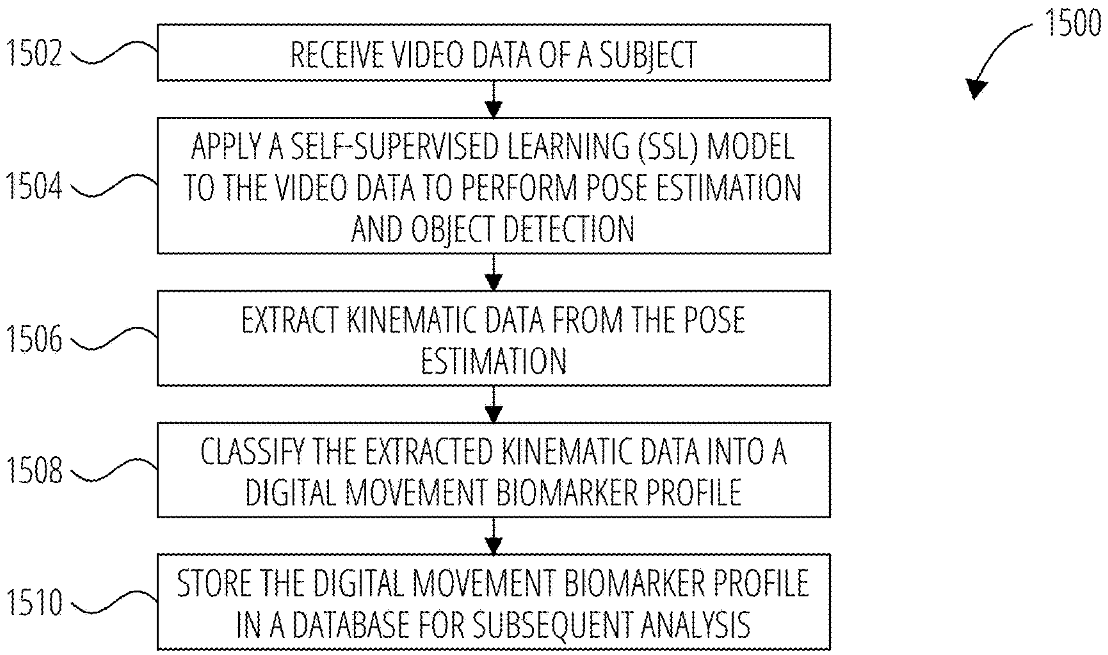
FIG. 15 illustrates a method for creating a digital movement biomarker in accordance with one embodiment.

Some examples include methods. With reference to FIG. 15, in operation 1502, method 1500 receives video data of a subject. In operation 1504, method 1500 applies a self-supervised learning (SSL) model to the video data to perform pose estimation and object detection. In operation 1506, method 1500 extracts kinematic data from the pose estimation. In operation 1508, method 1500 classifies the extracted kinematic data into a digital movement biomarker profile. In operation 1510, method 1500 stores the digital movement biomarker profile in a database for subsequent analysis.

Figure 16:
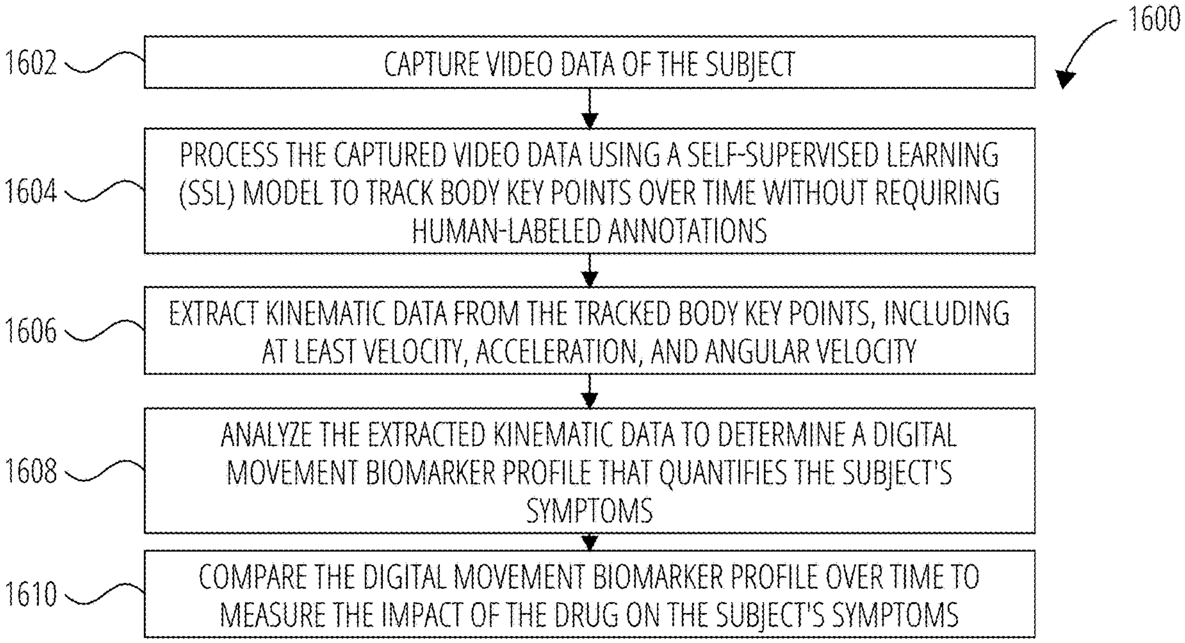
FIG. 16 illustrates a method for creating a digital movement biomarker for assessing an impact of a drug on a subject's symptoms, in accordance with one embodiment.

With reference to FIG. 16, in operation 1602, method 1600 captures video data of the subject. In operation 1604, method 1600 processes the captured video data using a self-supervised learning (SSL) model to track body key points over time without requiring human-labeled annotations. In operation 1606, method 1600 extracts kinematic data from the tracked body key points, including at least velocity, acceleration, and angular velocity. In operation 1608, method 1600 analyzes the extracted kinematic data to determine a digital movement biomarker profile that quantifies the subject's symptoms. In operation 1610, method 1600 compares the digital movement biomarker profile over time to measure the impact of the drug on the subject's symptoms.

Figure 17:
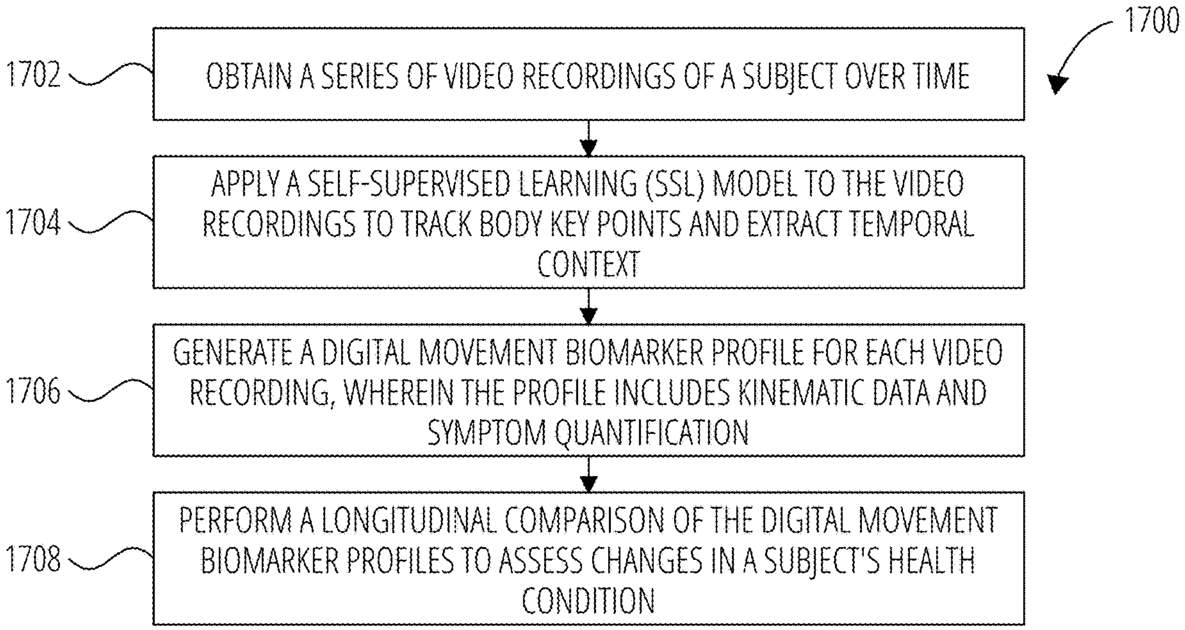
FIG. 17 illustrates a method in accordance with one embodiment.

With reference to FIG. 17, in operation 1702, method 1700 obtains a series of video recordings of a subject over time. In operation 1704, method 1700 applies a self-supervised learning (SSL) model to the video recordings to track body key points and extract temporal context. In operation 1706, method 1700 generates a digital movement biomarker profile for each video recording, wherein the profile includes kinematic data and symptom quantification. In operation 1708, method 1700 performs a longitudinal comparison of the digital movement biomarker profiles to assess changes in a subject's health condition.

Figure 18:
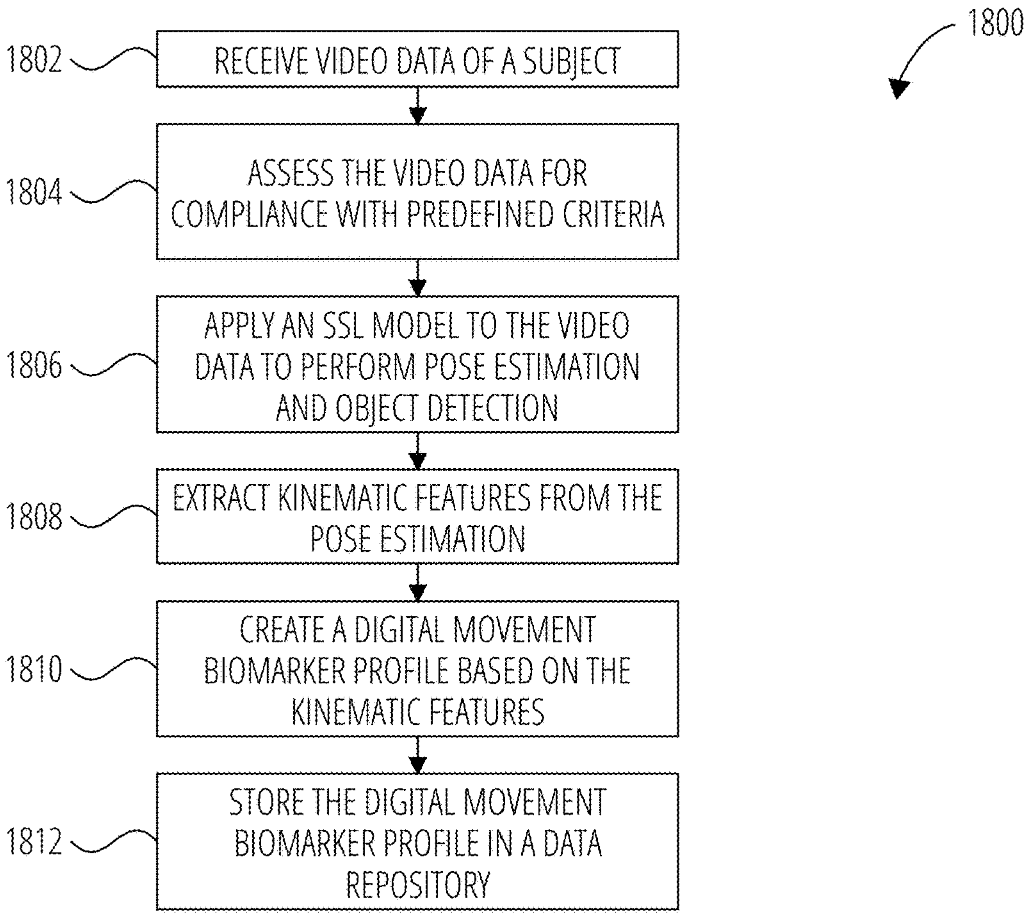
FIG. 18 illustrates a method for generating a self-supervised learning (SSL) digital movement biomarker, in accordance with one embodiment.

With reference to FIG. 18, in operation 1802, method 1800 receives video data of a subject. In operation 1804, method 1800 assesses the video data for compliance with predefined criteria. In operation 1806, method 1800 applies an SSL model to the video data to perform pose estimation and object detection. In operation 1808, method 1800 extracts kinematic features from the pose estimation. In operation 1810, method 1800 creates a digital movement biomarker profile based on the kinematic features. In operation 1812, method 1800 stores the digital movement biomarker profile in a data repository.

Figure 19:
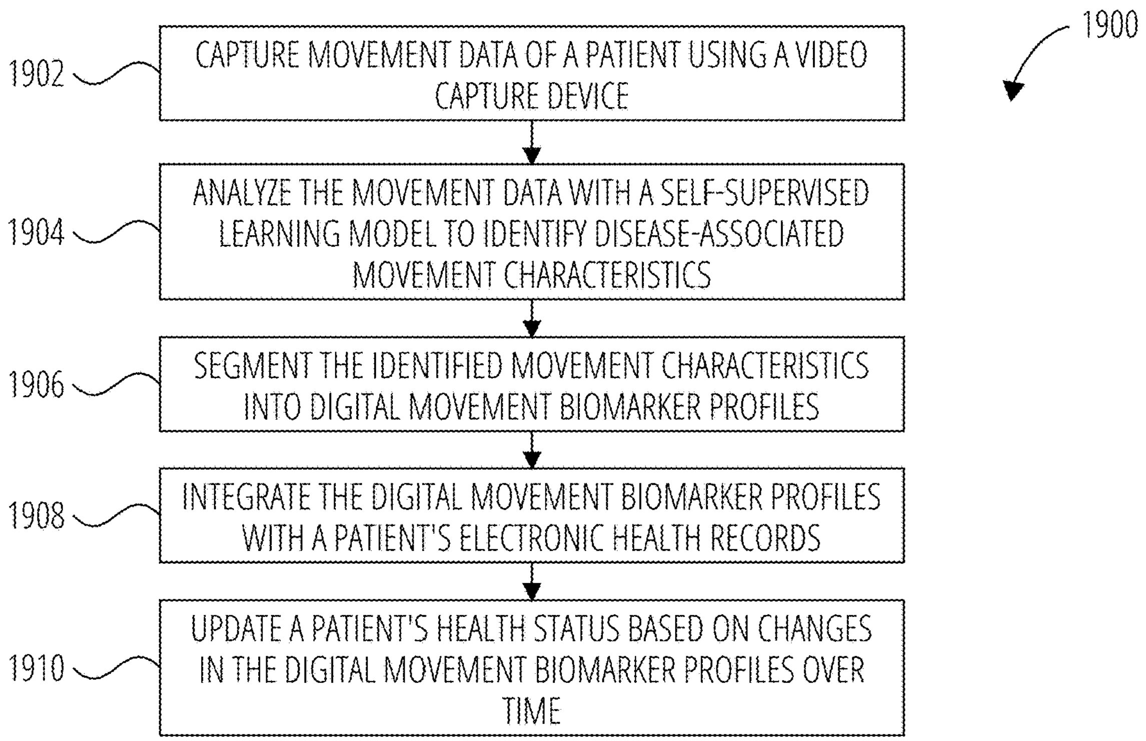
FIG. 19 illustrates a method for monitoring disease progression using digital movement biomarkers, in accordance with one embodiment.

With reference to FIG. 19, in operation 1902, method 1900 captures movement data of a patient using a video capture device. In operation 1904, method 1900 analyzes the movement data with a self-supervised learning model to identify disease-associated movement characteristics. In operation 1906, method 1900 segments the identified movement characteristics into digital movement biomarker profiles. In operation 1908, method 1900 integrates the digital movement biomarker profiles with a patient's electronic health records. In operation 1910, method 1900 updates a patient's health status based on changes in the digital movement biomarker profiles over time.

Figure 20:
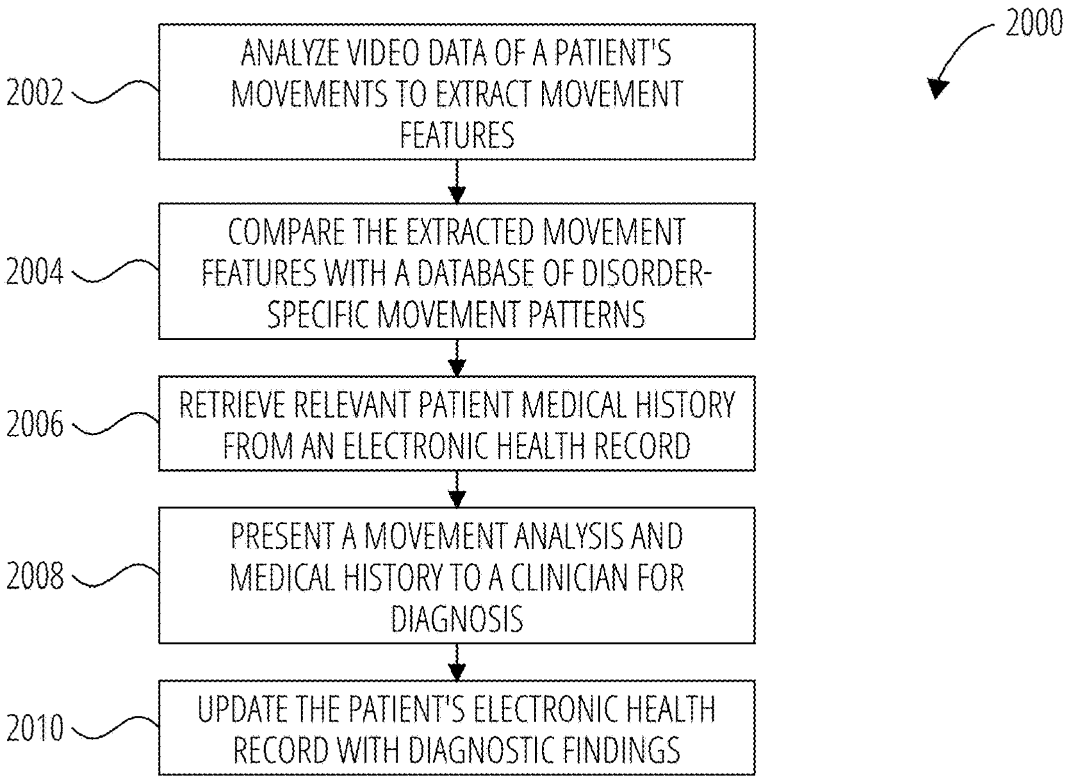
FIG. 20 illustrates a method for providing diagnostic support using SSL digital movement biomarker profiles, in accordance with one embodiment.

With reference to FIG. 20, in operation 2002, method 2000 analyzes video data of a patient's movements to extract movement features. In operation 2004, method 2000 compares the extracted movement features with a database of disorder-specific movement patterns. In operation 2006, method 2000 retrieves relevant patient medical history from an electronic health record. In operation 2008, method 2000 presents a movement analysis and medical history to a clinician for diagnosis. In operation 2010, method 2000 updates the patient's electronic health record with diagnostic findings.

Figure 21:
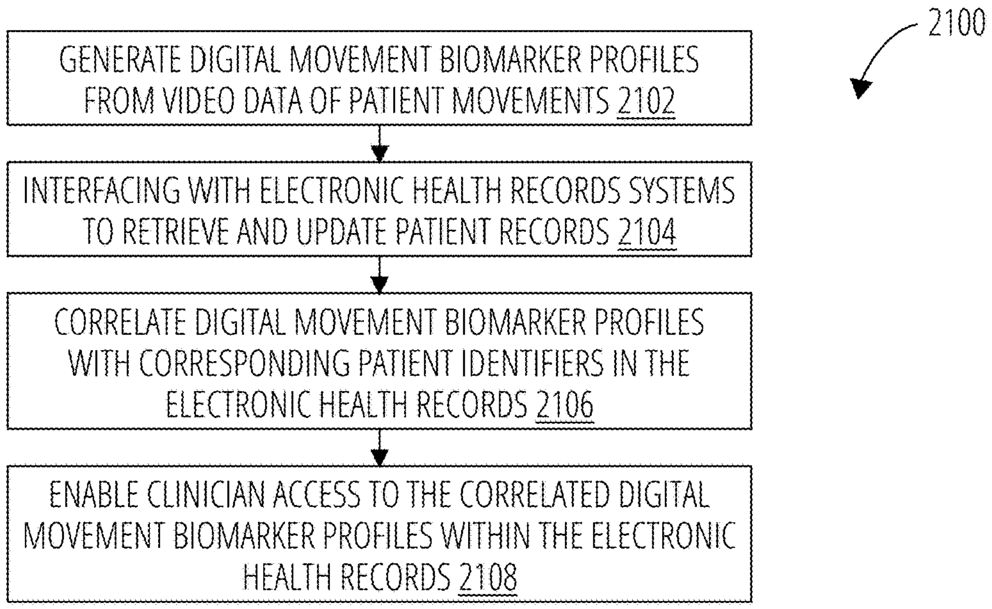
FIG. 21 illustrates a method for integrating SSL digital movement biomarker profiles with electronic health records, in accordance with one embodiment.

With reference to FIG. 21, in operation 2102, method 2100 generates digital movement biomarker profiles from video data of patient movements. In operation 2104, method 2100 interfacing with electronic health records systems to retrieve and update patient records. In operation 2106, method 2100 correlates digital movement biomarker profiles with corresponding patient identifiers in the electronic health records. In operation 2108, method 2100 enables clinician access to the correlated digital movement biomarker profiles within the electronic health records.

Figure 22:
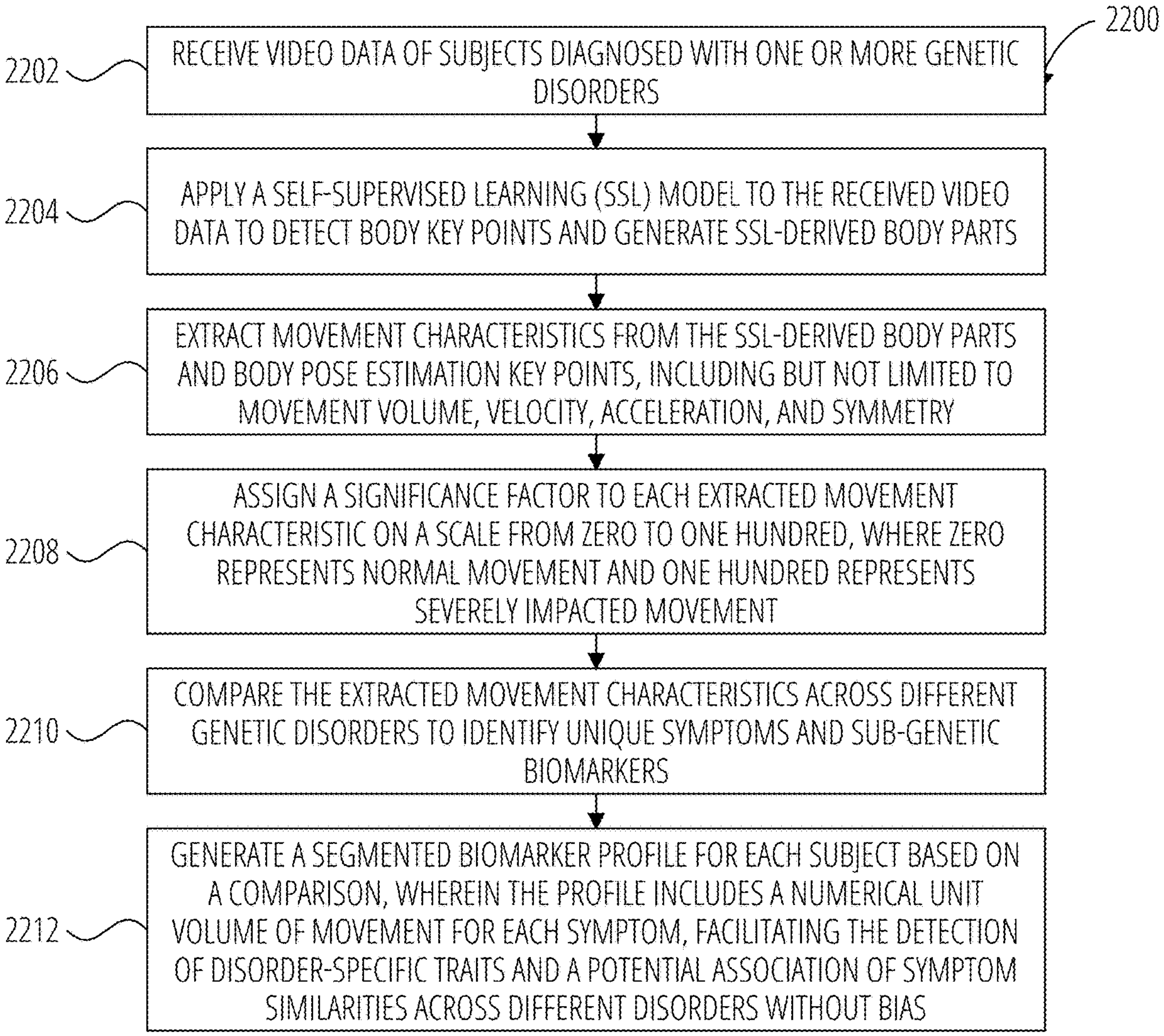
FIG. 22 illustrates a method for segmenting movement biomarkers in digital video analysis, in accordance with one embodiment.

With reference to FIG. 22, in operation 2202, method 2200 receives video data of subjects diagnosed with one or more genetic disorders. In operation 2204, method 2200 applies a self-supervised learning (SSL) model to the received video data to detect body key points and generate SSL-derived body parts. In operation 2206, method 2200 extracts movement characteristics from the SSL-derived body parts and body pose estimation key points, including but not limited to movement volume, velocity, acceleration, and symmetry. In operation 2208, method 2200 assigns a significance factor to each extracted movement characteristic on a scale from zero to one hundred, where zero represents normal movement and one hundred represents severely impacted movement. In operation 2210, method 2200 compares the extracted movement characteristics across different genetic disorders to identify unique symptoms and sub-genetic biomarkers. In operation 2212, method 2200 generates a segmented biomarker profile for each subject based on a comparison, wherein the profile includes a numerical unit volume of movement for each symptom, facilitating the detection of disorder-specific traits and a potential association of symptom similarities across different disorders without bias.

Figure 23:
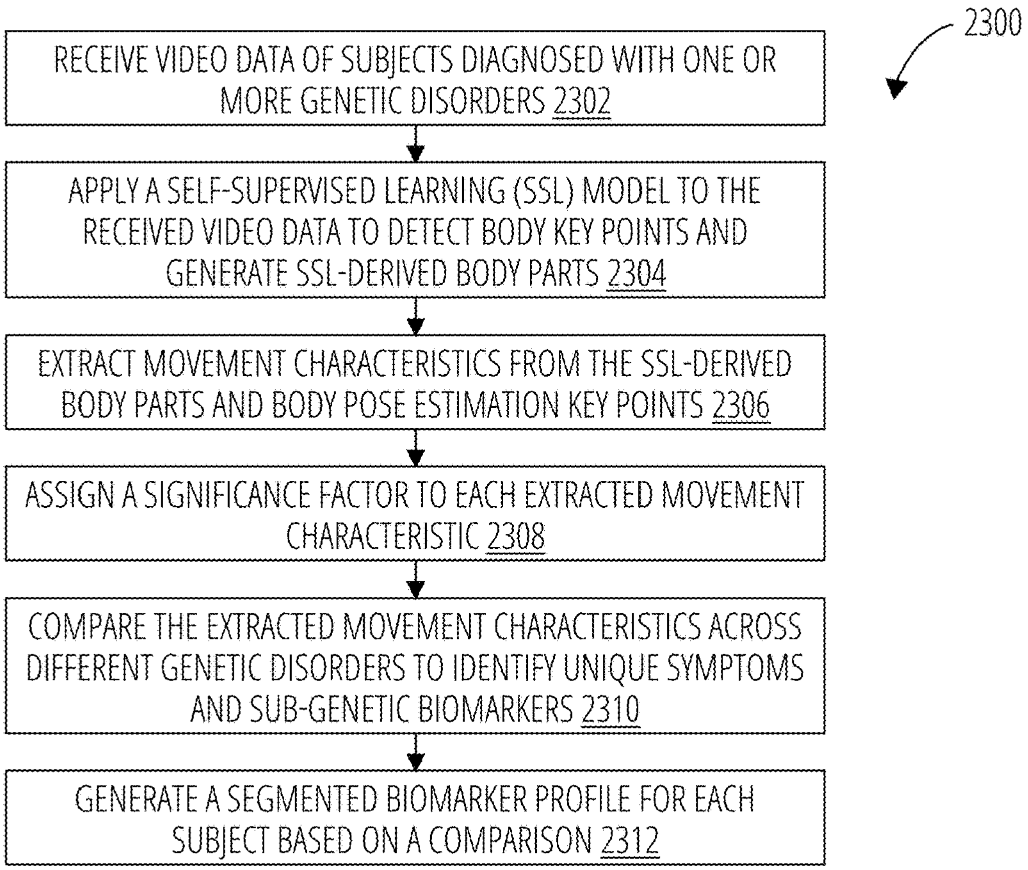
FIG. 23 illustrates a method for segmenting movement biomarkers in digital video analysis, in accordance with one embodiment.

With reference to FIG. 23, in operation 2302, method 2300 receives video data of subjects diagnosed with one or more genetic disorders. In operation 2304, method 2300 applies a self-supervised learning (SSL) model to the received video data to detect body key points and generate SSL-derived body parts. In operation 2306, method 2300 extracts movement characteristics from the SSL-derived body parts and body pose estimation key points. In operation 2308, method 2300 assigns a significance factor to each extracted movement characteristic. In operation 2310, method 2300 compares the extracted movement characteristics across different genetic disorders to identify unique symptoms and sub-genetic biomarkers. In operation 2312, method 2300 generates a segmented biomarker profile for each subject based on a comparison.

Figure 24:
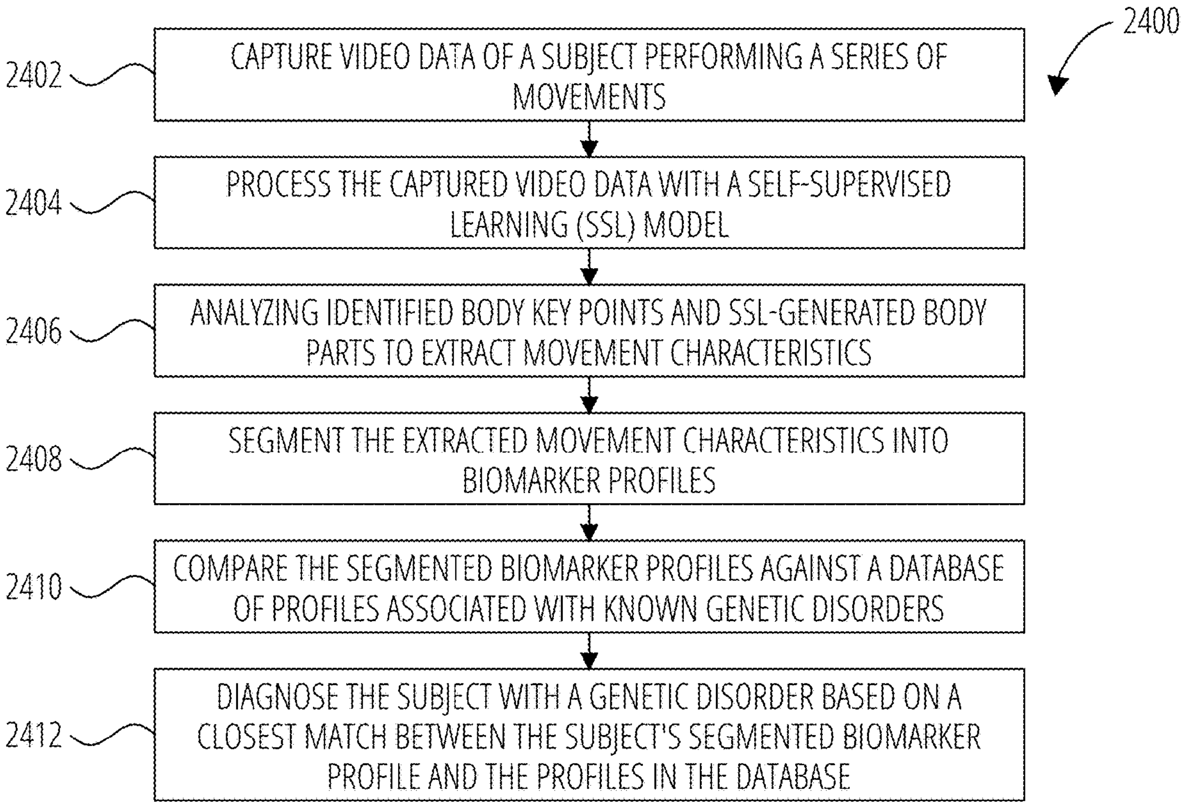
FIG. 24 illustrates a method for diagnosing genetic disorders using segmented movement biomarker profiles, in accordance with one embodiment.

With reference to FIG. 24, in operation 2402, method 2400 captures video data of a subject performing a series of movements. In operation 2404, method 2400 processes the captured video data with a self-supervised learning (SSL) model. In operation 2406, method 2400 analyzing identified body key points and SSL-generated body parts to extract movement characteristics. In operation 2408, method 2400 segments the extracted movement characteristics into biomarker profiles. In operation 2410, method 2400 compares the segmented biomarker profiles against a database of profiles associated with known genetic disorders. In operation 2412, method 2400 diagnoses the subject with a genetic disorder based on a closest match between the subject's segmented biomarker profile and the profiles in the database.

In summary, some examples thus include one or more of the following aspects.

In one aspect, a computing apparatus includes a processor. The computing apparatus also includes a memory storing instructions that, when executed by the processor, configure the apparatus to receive video data of a subject, apply a self-supervised learning (SSL) model to the video data to perform pose estimation and object detection, extract kinematic data from the pose estimation, classify the extracted kinematic data into a digital movement biomarker profile, and store the digital movement biomarker profile in a database for subsequent analysis.

In one aspect, a method for creating a digital movement biomarker, the method includes receiving video data of a subject, applying a self-supervised learning (SSL) model to the video data to perform pose estimation and object detection, extracting kinematic data from the pose estimation, classifying the extracted kinematic data into a digital movement biomarker profile, and storing the digital movement biomarker profile in a database for subsequent analysis.

In one aspect, a non-transitory computer-readable medium storing instructions that, when executed by a processor, cause the processor to perform a method for creating a digital movement biomarker, the method includes receiving video data of a subject, applying a self-supervised learning (SSL) model to the video data to perform pose estimation and object detection, extracting kinematic data from the pose estimation, classifying the extracted kinematic data into a digital movement biomarker profile, and storing the digital movement biomarker profile in a database for subsequent analysis.

In one aspect, a system for generating a digital movement biomarker from video data, includes a video capture device for recording movements of a subject, a computing device equipped with a self-supervised learning (SSL) algorithm capable of processing the video data to track movements and interactions of body parts over time, a kinematics analysis component for extracting objective measures from the tracked movements, and a biomarker generation component for creating a digital movement biomarker profile based on the objective measures, where the profile is indicative of a subject's health condition. The system may also include where the SSL algorithm is further configured to detect compliance issues in the video data based on predetermined criteria and provide feedback for video recapture if necessary. Other technical features may be readily apparent to one skilled in the art from the following figures, descriptions, and claims.

In one aspect, a method for creating a digital movement biomarker for assessing an impact of a drug on a subject's symptoms, includes capturing video data of the subject, processing the captured video data using a self-supervised learning (SSL) model to track body key points over time without requiring human-labeled annotations, extracting kinematic data from the tracked body key points, including at least velocity, acceleration, and angular velocity, analyzing the extracted kinematic data to determine a digital movement biomarker profile that quantifies the subject's symptoms, and comparing the digital movement biomarker profile over time to measure the impact of the drug on the subject's symptoms. The method may also include where the digital movement biomarker profile is used to diagnose a disease, determine symptom phenotypes, or measure disease severity. The method may also include where the SSL model is further configured to process video data from multiple subjects to identify common digital movement biomarker phenotypes indicative of potential candidates for a common medication. The method may also include where the SSL model adds temporal context to the video data by understanding a progression of body key points over time. The method may also include where the SSL model automatically classifies objects within the video to provide context to movements being analyzed. Other technical features may be readily apparent to one skilled in the art from the following figures, descriptions, and claims.

In one aspect, a computer-implemented method for longitudinal analysis of disease progression, includes obtaining a series of video recordings of a subject over time, applying a self-supervised learning (SSL) model to the video recordings to track body key points and extract temporal context, generating a digital movement biomarker profile for each video recording, where the profile includes kinematic data and symptom quantification, and performing a longitudinal comparison of the digital movement biomarker profiles to assess changes in a subject's health condition. The method may also include where the SSL model is trained to predict original, unmodified data based on altered versions of input data to grasp significant patterns and latent representations within the data. Other technical features may be readily apparent to one skilled in the art from the following figures, descriptions, and claims.

In one aspect, a system for generating a self-supervised learning (SSL) digital movement biomarker, includes a video input and process configuration component configured to receive video data of a subject, a compliance engine configured to assess the video data against predefined compliance criteria, a pose detection component including an SSL model trained to perform pose estimation and object detection on the video data, a kinematics component configured to derive kinematic features from the pose estimation, a digital movement biomarker profile generator configured to create a digital movement biomarker profile based on the kinematic features, and a data storage and access component configured to store the digital movement biomarker profile. The system may also include where the video input and process configuration component is further configured to convert video data from portrait to landscape orientation. The system may also include where the compliance engine is further configured to detect compliance issues including at least one of: body parts out of frame, excessive camera movement, poor lighting conditions, and presence of multiple people in the video. The system may also include where the SSL model is further trained to predict future body key point positions based on temporal context derived from the video data. The system may also include where the kinematics component is configured to calculate kinematic features including at least one of: velocity, acceleration, angular velocity, and angular acceleration for each body part and joint. The system may also include where the digital movement biomarker profile generator is further configured to assign a significance factor to each movement characteristic, with a scale ranging from a lower score, indicating normal movement, to a higher score, indicating severely impacted movement. Other technical features may be readily apparent to one skilled in the art from the following figures, descriptions, and claims.

In one aspect, a system for monitoring disease progression using digital movement biomarkers, includes a video capture device for recording movement data of a patient, a processing unit equipped with a self-supervised learning model for analyzing the movement data, a feature extraction component for identifying movement characteristics associated with a disease, a classification engine for segmenting the movement characteristics into digital movement biomarker profiles, and an integration interface for correlating the digital movement biomarker profiles with electronic health records. The system may also include where the video capture device includes a high-definition camera capable of capturing video at a frame rate suitable for detailed movement analysis. The system may also include where the processing unit is further configured to apply machine learning algorithms for temporal and spatial feature extraction from the movement data. The system may also include where the classification engine utilizes a neural network specifically trained to recognize movement patterns associated with a predefined set of disorders. The system may also include where the integration interface includes a user interface for clinicians to manually review and adjust the digital movement biomarker profiles before integration with electronic health records. The system may also include where the system further includes a visualization component configured to generate visual representations of the digital movement biomarker profiles for clinical interpretation. Other technical features may be readily apparent to one skilled in the art from the following figures, descriptions, and claims.

In one aspect, a method for generating a self-supervised learning (SSL) digital movement biomarker, includes receiving video data of a subject, assessing the video data for compliance with predefined criteria, applying an SSL model to the video data to perform pose estimation and object detection, extracting kinematic features from the pose estimation, creating a digital movement biomarker profile based on the kinematic features, and storing the digital movement biomarker profile in a data repository. The method may also include further includes converting the video data from portrait to landscape orientation prior to assessing compliance. The method may also include where assessing the video data for compliance includes detecting at least one of: incomplete capture of body parts, excessive camera movement, inadequate lighting, and a presence of additional individuals in the video. The method may also include further includes training the SSL model to recognize and classify objects within the video data to provide context to a movement analysis. The method may also include where extracting kinematic features includes calculating at least one of: distance, velocity, acceleration, symmetry, and repetition of body movements. The method may also include further includes assigning a significance factor to each identified movement characteristic based on a scale from zero to one hundred. Other technical features may be readily apparent to one skilled in the art from the following figures, descriptions, and claims.

In one aspect, a method for monitoring disease progression using digital movement biomarkers, includes capturing movement data of a patient using a video capture device, analyzing the movement data with a self-supervised learning model to identify disease-associated movement characteristics, segmenting the identified movement characteristics into digital movement biomarker profiles, integrating the digital movement biomarker profiles with a patient's electronic health records, and updating a patient's health status based on changes in the digital movement biomarker profiles over time. The method may also include further includes utilizing a high-definition video capture device to record the movement data at a frame rate suitable for detailed kinematic analysis. The method may also include where analyzing the movement data includes applying machine learning algorithms to extract temporal and spatial features indicative of disease progression. The method may also include further includes employing a neural network trained to differentiate between movement patterns of various disorders for a classification of the digital movement biomarker profiles. The method may also include further includes providing a user interface for clinicians to review and adjust the digital movement biomarker profiles prior to integration with electronic health records. The method may also include further includes generating visual representations of the digital movement biomarker profiles to aid clinicians in an interpretation and diagnosis of disorders. Other technical features may be readily apparent to one skilled in the art from the following figures, descriptions, and claims.

In one aspect, a diagnostic support system for detecting disorders, includes a video processing component configured to receive and analyze video data of a patient's movements, a diagnostic engine configured to compare extracted movement features against a database of disorder-specific movement patterns, an EHR integration component configured to retrieve and display relevant patient medical history from an electronic health record, and a decision support interface configured to present combined movement analysis and medical history to a clinician for diagnosis. The system may also include where the video processing component includes a self-supervised learning (SSL) model for enhanced movement feature extraction. The system may also include where the diagnostic engine is further configured to generate a likelihood score indicating a probability of a disorder based on the movement features. The system may also include where the EHR integration component is further configured to update the patient's electronic health record with diagnostic findings. The system may also include where the decision support interface provides visual aids including graphs, charts, and heat maps of the movement analysis. The system may also include where the system further includes a notification component configured to alert clinicians to significant changes in the patient's movement patterns over time. Other technical features may be readily apparent to one skilled in the art from the following figures, descriptions, and claims.

In one aspect, a system for integrating SSL digital movement biomarker profiles with electronic health records, includes a biomarker profile generation component configured to process video data and generate digital movement biomarker profiles, an EHR communication component configured to interface with electronic health records systems using standardized healthcare data exchange protocols, a data correlation component configured to associate digital movement biomarker profiles with corresponding patient identifiers in the electronic health records, and a profile access component configured to enable clinician access to the correlated digital movement biomarker profiles within the electronic health records. The system may also include where the biomarker profile generation component utilizes a machine learning model trained on a dataset of known disorder-specific movement patterns. The system may also include where the EHR communication component employs Health Level Seven (HL7) or Fast Healthcare Interoperability Resources (FHIR) standards for data exchange. The system may also include where the data correlation component further includes a matching algorithm to ensure accurate association of biomarker profiles with patient records. The system may also include where the profile access component includes a user interface designed to display biomarker profiles in conjunction with clinical notes and lab results. The system may also include where the system further includes a data security component configured to encrypt digital movement biomarker profiles during storage and transmission. Other technical features may be readily apparent to one skilled in the art from the following figures, descriptions, and claims.

In one aspect, a method for providing diagnostic support using SSL digital movement biomarker profiles, includes analyzing video data of a patient's movements to extract movement features, comparing the extracted movement features with a database of disorder-specific movement patterns, retrieving relevant patient medical history from an electronic health record, presenting a movement analysis and medical history to a clinician for diagnosis, and updating the patient's electronic health record with diagnostic findings. The method may also include where analyzing video data includes applying a self-supervised learning model to identify disorder-specific movement features. The method may also include further includes generating a likelihood score based on a comparison of movement features with the disorder-specific patterns. The method may also include further includes providing visual aids to assist the clinician in interpreting the movement analysis. The method may also include further includes alerting the clinician to significant changes in the patient's movement patterns over time. The method may also include where updating the patient's electronic health record includes encrypting the diagnostic findings prior to storage. Other technical features may be readily apparent to one skilled in the art from the following figures, descriptions, and claims.

In one aspect, a method for integrating SSL digital movement biomarker profiles with electronic health records, includes generating digital movement biomarker profiles from video data of patient movements, interfacing with electronic health records systems to retrieve and update patient records, correlating digital movement biomarker profiles with corresponding patient identifiers in the electronic health records, and enabling clinician access to the correlated digital movement biomarker profiles within the electronic health records. The method may also include where generating digital movement biomarker profiles includes training a machine learning model on a dataset of known disorder-specific movement patterns. Other technical features may be readily apparent to one skilled in the art from the following figures, descriptions, and claims.

In one aspect, a method for segmenting movement biomarkers in digital video analysis, includes receiving video data of subjects diagnosed with one or more genetic disorders, applying a self-supervised learning (SSL) model to the received video data to detect body key points and generate SSL-derived body parts, extracting movement characteristics from the SSL-derived body parts and body pose estimation key points, including but not limited to movement volume, velocity, acceleration, and symmetry, assigning a significance factor to each extracted movement characteristic on a scale from zero to one hundred, where zero represents normal movement and one hundred represents severely impacted movement, comparing the extracted movement characteristics across different genetic disorders to identify unique symptoms and sub-genetic biomarkers, and generating a segmented biomarker profile for each subject based on a comparison, where the profile includes a numerical unit volume of movement for each symptom, facilitating the detection of disorder-specific traits and a potential association of symptom similarities across different disorders without bias.

In one aspect, a system for generating segmented digital movement biomarker profiles for genetic disorders, includes an input component configured to receive video data and optional genetic and clinical data of subjects, a pose detection component utilizing a self-supervised learning (SSL) model to analyze the video data and identify body key points and SSL-generated body parts, a kinematics component for measuring movement characteristics derived from the pose detection component, a classification engine for assigning significance factors to the measured movement characteristics and for identifying unique symptoms and sub-genetic biomarkers across and within genetic disorders, a biomarker segmentation component for creating segmented biomarker profiles that encapsulate all classified movement symptoms, represented by a numerical unit volume of movement, and a data storage and access component for securely storing the segmented biomarker profiles and facilitating their retrieval for analysis, where the system is configured to enable a comparison of subject traits across disorders and the detection of disorders based on traits, thereby providing a de-siloed and self-learned approach to symptom measurement.

In one aspect, a computer-implemented method for diagnosing genetic disorders using segmented movement biomarker profiles, includes capturing video data of a subject performing a series of movements, processing the captured video data with a self-supervised learning (SSL) model to identify body key points and derive SSL-generated body parts, analyzing the identified body key points and SSL-generated body parts to extract movement characteristics and calculate kinematic data, segmenting the extracted movement characteristics into biomarker profiles based on a presence and severity of symptoms, where each symptom is quantified by a numerical unit volume of movement, comparing the segmented biomarker profiles against a database of profiles associated with known genetic disorders to identify matching patterns, and diagnosing the subject with a genetic disorder based on a closest match between the subject's segmented biomarker profile and the profiles in the database, where the method enables an identification of disorder-specific traits and the association of symptom similarities across different disorders, contributing to personalized medicine and targeted therapy development.

In one aspect, a method for segmenting movement biomarkers in digital video analysis, includes receiving video data of subjects diagnosed with one or more genetic disorders, applying a self-supervised learning (SSL) model to the received video data to detect body key points and generate SSL-derived body parts, extracting movement characteristics from the SSL-derived body parts and body pose estimation key points, assigning a significance factor to each extracted movement characteristic, comparing the extracted movement characteristics across different genetic disorders to identify unique symptoms and sub-genetic biomarkers, generating a segmented biomarker profile for each subject based on a comparison.

In one aspect, a system for generating segmented digital movement biomarker profiles for genetic disorders, includes an input component configured to receive video data and optional genetic and clinical data of subjects, a pose detection component utilizing a self-supervised learning (SSL) model to analyze the video data, a kinematics component for measuring movement characteristics derived from the pose detection component, a classification engine for assigning significance factors to the measured movement characteristics, a biomarker segmentation component for creating segmented biomarker profiles, a data storage and access component for securely storing the segmented biomarker profiles.

In one aspect, a computer-implemented method for diagnosing genetic disorders using segmented movement biomarker profiles, includes capturing video data of a subject performing a series of movements, processing the captured video data with a self-supervised learning (SSL) model, analyzing identified body key points and SSL-generated body parts to extract movement characteristics, segmenting the extracted movement characteristics into biomarker profiles, comparing the segmented biomarker profiles against a database of profiles associated with known genetic disorders, diagnosing the subject with a genetic disorder based on a closest match between the subject's segmented biomarker profile and the profiles in the database. The method may also include where interfacing with electronic health records systems includes using HL7 or FHIR protocols for data exchange. The method may also include further includes employing a matching algorithm to accurately associate biomarker profiles with patient records. The method may also include further includes displaying biomarker profiles alongside clinical notes and lab results within electronic health records. The method may also include further includes encrypting digital movement biomarker profiles during storage and transmission to ensure data security. Other technical features may be readily apparent to one skilled in the art from the following figures, descriptions, and claims.

What is claimed is:

1. A system for generating a self-supervised learning (SSL) digital movement biomarker, comprising:
- a video input and process configuration component configured to receive video data of a subject;
- a compliance engine configured to assess the video data against predefined compliance criteria;
- a pose detection component including an SSL model to perform pose estimation and object detection on the video data;
- a kinematics component configured to derive kinematic features from the pose estimation;
- a digital movement biomarker profile generator configured to create a digital movement biomarker profile based on the kinematic features; and
- a data storage and access component configured to store the digital movement biomarker profile, wherein the digital movement biomarker profile is generated based on movement characteristics identified by the SSL model from the subject's movement in relation to objects detected and segmented within the video environment, independently of pre defined clinical outcome measures.

2. The system of claim 1, wherein the video input and process configuration component is further configured to convert video data from portrait to landscape orientation.

3. The system of claim 2, wherein the compliance engine is further configured to detect compliance issues including at least one of: body parts out of frame, excessive camera movement, poor lighting conditions, and presence of multiple people in the video.

4. The system of claim 3, wherein the SSL model is further trained to predict future body key point positions based on temporal context derived from the video data.

5. The system of claim 4, wherein the kinematics component is configured to calculate kinematic features including at least one of: velocity, acceleration, angular velocity, and angular acceleration for each body part and joint.

6. The system of claim 5, wherein the digital movement biomarker profile generator is further configured to assign a significance factor to each movement characteristic, with a scale ranging from a lower score, indicating normal movement, to a higher score, indicating severely impacted movement.

7. A method for generating a self-supervised learning (SSL) digital movement biomarker, comprising:
- receiving video data of a subject;
- assessing the video data for compliance with predefined criteria;
- applying an SSL model to the video data to perform pose estimation and object detection;
- extracting kinematic features from the pose estimation;
- creating a digital movement biomarker profile based at least in art on movement characteristics identified by the SSL model from the subject's movement in relation to objects detected and segmented within the video environment, and storing the digital movement biomarker in a data repository wherein the digital movement biomarker profile is generated independently of pre-defined clinical outcome measures.

8. The method of claim 7, further comprising converting the video data from portrait to landscape orientation prior to assessing compliance.

9. The method of claim 8, wherein assessing the video data for compliance includes detecting at least one of: incomplete capture of body parts, excessive camera movement, inadequate lighting, and a presence of additional individuals in the video.

10. The method of claim 9, further comprising training the SSL model to recognize and classify objects within the video data to provide context to a movement analysis.

11. The method of claim 10, wherein extracting kinematic features includes calculating at least one of: distance, velocity, acceleration, symmetry, and repetition of body movements.

12. The method of claim 11, further comprising assigning a significance factor to each identified movement characteristic based on a scale from zero to one hundred.

13. The method of claim 12, further comprising providing a user interface for clinicians to review and adjust the digital movement biomarker profiles prior to integration with electronic health records.

14. The method of claim 13, further comprising generating visual representations of the digital movement biomarker profiles to aid clinicians in an interpretation and diagnosis of disorders.

15. A system for integrating SSL digital movement biomarker profiles with electronic health records, comprising:

a biomarker profile generation component configured to process video data and generate digital movement biomarker profiles based on movement characteristics identified by an SSL model from a subject's movement in relation to objects detected and segmented within the video environment, independently of pre-defined clinical outcome measures;

an EHR communication component configured to interface with electronic health records systems using standardized healthcare data exchange protocols;

a data correlation component configured to associate digital movement biomarker profiles with corresponding patient identifiers in the electronic health records;

a profile access component configured to enable clinician access to the correlated digital movement biomarker profiles within the electronic health records; and wherein the biomarker profile generation component utilizes a self-supervised trained without reliance on pre-defined clinical outcome measures.

16. The system of claim 15, wherein the EHR communication component employs Health Level Seven (HL7) or Fast Healthcare Interoperability Resources (FHIR) standards for data exchange.

17. The system of claim 16, wherein the data correlation component further includes a matching algorithm to ensure accurate association of biomarker profiles with patient records.

18. The system of claim 17, wherein the profile access component includes a user interface designed to display biomarker profiles in conjunction with clinical notes and lab results.

19. The system of claim 18, wherein the system further comprises a data security component configured to encrypt digital movement biomarker profiles during storage and transmission.

* * * * *